United States Patent
Strzelecki et al.

(10) Patent No.: US 12,229,927 B2
(45) Date of Patent: Feb. 18, 2025

(54) METAL ARTIFACT REDUCTION IN COMPUTED TOMOGRAPHY

(71) Applicant: SIEMENS HEALTHINEERS INTERNATIONAL AG, Palo Alto, CA (US)

(72) Inventors: Adam Michal Strzelecki, Daettwil (CH); Igor Peterlik, Kuenten (CH); Dieter Marc Seghers, Zürich (CH); Mathieu Plamondon, Glattburg (CH); Mathias Lehmann, Zürich (CH); Pascal Paysan, Basel (CH); Alexander Heinz, Lörrach (DE)

(73) Assignee: SIEMENS HEALTHINEERS INTERNATIONAL AG (CH)

(*) Notice: Subject to any disclaimer, the term of this patent is extended or adjusted under 35 U.S.C. 154(b) by 291 days.

(21) Appl. No.: 17/546,081

(22) Filed: Dec. 9, 2021

(65) Prior Publication Data

US 2023/0095240 A1    Mar. 30, 2023

Related U.S. Application Data

(60) Provisional application No. 63/250,050, filed on Sep. 29, 2021.

(51) Int. Cl.
*G06T 5/77* (2024.01)
*A61B 6/00* (2006.01)
(Continued)

(52) U.S. Cl.
CPC .............. *G06T 5/77* (2024.01); *A61B 6/5258* (2013.01); *G06T 5/50* (2013.01); *G06T 11/008* (2013.01);
(Continued)

(58) Field of Classification Search
CPC ... G06T 5/77; G06T 5/50; G06T 2207/20212; G06T 2207/10081; G06T 11/008
See application file for complete search history.

(56) References Cited

U.S. PATENT DOCUMENTS 6,721,387 B1    4/2004   Naidu et al.
7,636,461 B2   12/2009   Spies et al.
(Continued)

OTHER PUBLICATIONS

Zhang et al. "Reducing metal artifacts in cone-beam CT images by preprocessing projection data." International Journal of Radiation Oncology, Biology, Physics 67.3 (2007): 924-932 (Year: 2007).*
(Continued)

*Primary Examiner* — Sumati Lefkowitz
*Assistant Examiner* — Michael Adam Shariff
(74) *Attorney, Agent, or Firm* — SU IP CONSULTING

(57) ABSTRACT

A computer-implemented method for modifying X-ray projection images of a subject region includes: generating a set of combined two-dimensional (2D) projections of a subject region, wherein each combined 2D projection includes one or more mask-bordering pixels and one or more mask-edge pixels; forming a three-dimensional (3D) matrix of the set of combined 2D projections; based on the 3D matrix, generating a linear algebraic system for determining pixel values for pixels indicated in a set of 2D projection metal masks, wherein a first change in slope of pixel value associated with a mask-edge pixel of a combined 2D projection is constrained to equal a second change in slope of pixel value associated with a mask-bordering pixel of a combined 2D projection; determining values for a variable vector of the linear algebraic system; and generating a set of inpainted 2D projections by modifying initial 2D projections with values for the variable vector.

20 Claims, 13 Drawing Sheets

(51) Int. Cl.
  *A61N 5/10* (2006.01)
  *G06T 5/50* (2006.01)
  *G06T 11/00* (2006.01)

(52) U.S. Cl.
  CPC ...... *A61N 5/10* (2013.01); *G06T 2207/10081* (2013.01); *G06T 2207/20212* (2013.01)

(56) References Cited

U.S. PATENT DOCUMENTS

| | | |
|---|---|---|
| 8,503,750 B2 | 8/2013 | Benson et al. |
| 2011/0081071 A1 | 4/2011 | Benson et al. |
| 2015/0029178 A1 | 1/2015 | Claus et al. |
| 2017/0270687 A1 | 9/2017 | Manhart |
| 2018/0137658 A1 | 5/2018 | Zhang et al. |
| 2022/0207794 A1 | 6/2022 | Sarti et al. |
| 2023/0100798 A1 | 3/2023 | Peterlik et al. |

OTHER PUBLICATIONS

The Extended European Search Report, application No. 22198774.6, Feb. 27, 2023.
Yongbin Zhang et al., "Reducing Metal Artifacts in Cone-Beam CT Images by Preprocessing Projection Data", International Journal of Radiation: Oncology Biology Physics, Feb. 9, 2007, pp. 924-932, vol. 67, No. 3.
S.B. Damelin et al., "On Surface Completion and Image Inpainting by Biharmonic Functions: Numerical Aspects", Arxiv.org, Cornell University Library, 201 Olin Library Cornell University Ithaca, Jul. 20, 2017.
Julia Hamer et al., "Modified Eulers Elastica Inpainting for Metal Artifact Reduction in CT", Proceedings does workshops, Jan. 2012, pp. 310-315.
Mark Korpics, BS et al., "Metal Artifact Reduction in Cone-Beam Computed Tomography for Head and Neck Radiotherapy", Technology in Cancer Research & Treatment, Dec. 2016, pp. NP88-NP94, vol. 15, No. 6.
The Extended European Search Report, application No. 22198789.4, Jan. 26, 2023.
Seemeen Karimi, "Metal Artifact Reduction in Computed Tomography", Retrieved on Dec. 16, 2022 from the Internet at <URL: https://escholarship.org/content/qt9w55m91h/qt9w55m91h.pdf>, Jan. 1, 2014, XP093009091.
S. Lee et al., "Automated CNN-Based Tooth Segmentation in Cone-Beam CT for Dental Implant Planning", Retrieved on Mar. 17, 2020, IEEE Access, Feb. 24, 2020, vol. 8, XP011778735.
Non-Published Commonly Owned U.S. Appl. No. 17/546,080, filed Dec. 9, 2021, 47 pages, Siemens Healthineers International AG.

\* cited by examiner

METAL ARTIFACT REDUCTION IN COMPUTED TOMOGRAPHY

CROSS-REFERENCE TO RELATED APPLICATION

The present application claims the benefit of U.S. Provisional Application No. 63/250,050, filed Sep. 29, 2021. The aforementioned U.S. Provisional Application, including any appendices or attachments thereof, is hereby incorporated by reference in its entirety.

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on the planning target volume that spares the surrounding normal tissue from receiving doses above specified tolerances, thereby minimizing risk of damage to healthy tissue. Prior to the delivery of radiation therapy, an imaging system is typically employed to provide a three-dimensional image of the target tissue and surrounding area. From such imaging, the size and mass of the target tissue can be estimated, a planning target volume determined, and an appropriate treatment plan generated.

So that the prescribed dose is correctly supplied to the planning target volume (i.e., the target tissue) during radiation therapy, the patient should be correctly positioned relative to the linear accelerator that provides the radiation therapy. Typically, dosimetric and geometric data are checked before and during the treatment, to ensure correct patient placement and that the administered radiotherapy treatment matches the previously planned treatment. This process is referred to as image guided radiation therapy (IGRT), and involves the use of an imaging system to view target tissues immediately before or while radiation treatment is delivered to the planning target volume. IGRT incorporates imaging coordinates from the treatment plan to ensure the patient is properly aligned for treatment in the radiation therapy device.

SUMMARY

According to various embodiments, a reconstructed volume of a subject region is processed so that visual artifacts in the reconstructed volume are reduced. Specifically, in some embodiments, novel inpainting, blending, and/or metal object extraction techniques are employed to reduce or eliminate visual artifacts that occur in a reconstructed volume of an anatomical region that includes one or more metal objects, such as fiducials or dental/orthopedic components.

In some embodiments, an automated process is employed for extracting location information for metal objects disposed within a scanned anatomical region. In the automated process, patient anatomy in a scanned region is identified and classified, and the type of metal present in the scanned region is determined. Based on the patient anatomy and type of metal, accurate thresholding values are determined that facilitate generation of projection metal object masks for the scanned region, and such masks enable the reduction of visual artifacts in a reconstructed volume.

In some embodiments, a novel method is employed for inpainting the portions of two-dimensional (2D) projections of a subject region that are blocked by metal objects. In the method, sharp transitions between the values of inpainted pixels and pixels of known value are mathematically constrained using a harmonic function, both within the same 2D projection (intra-projection consistency) and between adjacent 2D projections (inter-projection consistency).

In some embodiments, a novel blending method is employed for blending image information from multiple types of 2D projections of a subject region (e.g., initial projection images, projection metal masks, flattened projections, and/or inpainted projections). For example, in one such embodiment, regions within initial (not inpainted) projection images of a subject region are indicated by projection metal masks, and these regions are modified with image information from flattened projections of the subject region that are generated via a conventional tissue-flattening process. In the novel blending method, sharp transitions between the values of pixels in the modified regions and of pixels outside the modified regions are mathematically constrained using a harmonic function, both within the same 2D projection (intra-projection consistency) and between adjacent 2D projections (inter-projection consistency).

In some embodiments, a novel blending method is employed for restoring metal objects within a reconstructed volume of a subject region. In the novel blending method, a non-binary metal mask is employed when blending metal object information with a reconstructed volume that is generated via the removal of metal objects. The novel blending method improves the appearance of metal objects when returned to the reconstructed volume, since the non-binary metal mask causes edge voxels of metal regions to appear smooth in the final reconstructed volume.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
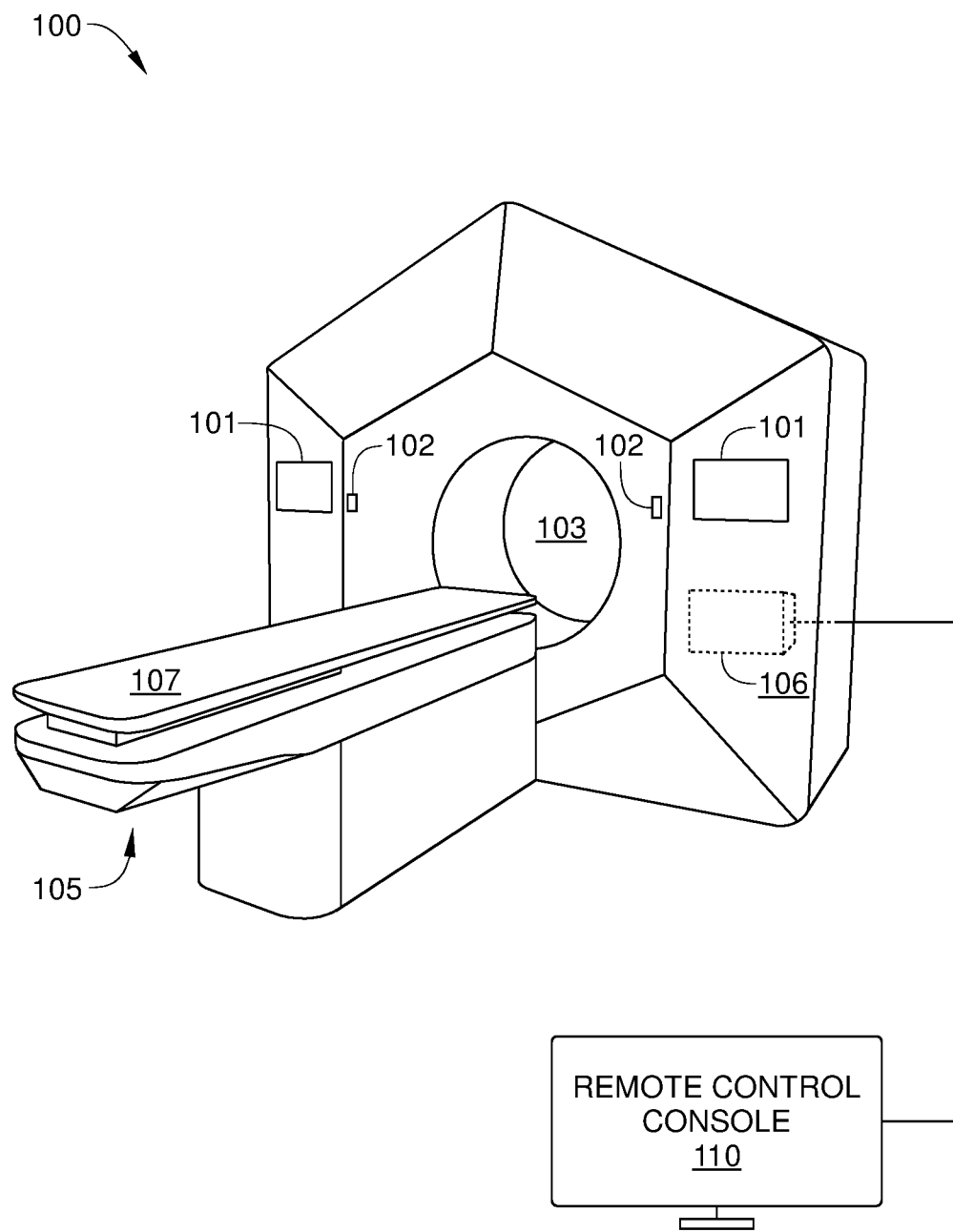
FIG. 1 is a perspective view of a radiation therapy system that can beneficially implement various aspects of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

Introduction

Image guided radiation therapy (IGRT) is used to treat tumors in areas of the body that are subject to voluntary movement, such as the lungs, or involuntary movement, such as organs affected by peristalsis, gas motion, muscle contraction and the like. IGRT involves the use of an imaging system to view target tissues (also referred to as the "target volume") immediately before or while radiation treatment is delivered thereto. In IGRT, image-based coordinates of the target volume from a previously determined treatment plan are compared to image-based coordinates of the target volume determined immediately before or during the application of the treatment beam. In this way, changes in the surrounding organs at risk and/or motion or deformation of the target volume relative to the radiation therapy system can be detected. Consequently, dose limits to organs at risk are accurately enforced based on the daily position and shape, and the patient's position and/or the treatment beam can be adjusted to more precisely target the radiation dose to the tumor. For example, in pancreatic tumor treatments, organs at risk include the duodenum and stomach. The shape and relative position of these organs at risk with respect to the target volume can vary significantly from day-to-day. Thus, accurate adaption to the shape and relative position of such organs at risk enables escalation of the dose to the target volume and better therapeutic results.

For reconstructions of patient anatomy surrounding a target volume, computed tomography (CT) or cone-beam computed tomography (CBCT) is often employed for generating the two-dimensional (2D) projections images from which the patient anatomy is reconstructed. In such image reconstruction, metal objects inside a scanned anatomical region are a significant source of visual artifacts that negatively impact the quality of images generated from the reconstructed anatomical region. These visual artifacts can be caused by one or more phenomena related to the presence of metals in the scanned anatomical region, including beam hardening in polychromatic CT and CBCT beams, photon starvation by larger metal components, scatter of imaging X-rays that impact metal components, and motion of metal objects during CT or CBCT acquisition. Such visual artifacts typically degrade the quality of the reconstruction and the ability to accurately detect the current location of a target volume and/or critical structures adjacent to the target volume.

According to various embodiments, a reconstructed volume of a region of patient anatomy is processed so that metal-related visual artifacts in the reconstructed volume are reduced. Specifically, in some embodiments, one or more of an automated metal extraction process, a novel method for inpainting portions of 2D projections, a novel blending method for blending image information from multiple types of 2D projections, and/or a novel blending method for restoring metal objects within a reconstructed volume are employed to reduce visual artifacts in a reconstructed volume.

System Overview

FIG. 1 is a perspective view of a radiation therapy system 100 that can beneficially implement various aspects of the present disclosure. Radiation therapy (RT) system 100 is a radiation system configured to detect intra-fraction motion in near-real time using X-ray imaging techniques. Thus, RT system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) that generates a megavolt (MV) treatment beam of high energy X-rays, one or more kilovolt (kV) X-ray sources, one or more X-ray imagers, and, in some embodiments, an MV electronic portal imaging device (EPID). By way of example, radiation therapy system 100 is described herein configured with a circular gantry. In other embodiments, radiation therapy system 100 can be configured with a C-gantry capable of infinite rotation via a slip ring connection.

Generally, RT system 100 is capable of kV imaging of a target volume immediately prior to or during application of an MV treatment beam, so that an IGRT and/or an intensity-modulated radiation therapy (IMRT) process can be performed using X-ray imaging. RT system 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. RT system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as button and/or switches, that enable a user to operate base positioning assembly 105 to automatically and precisely position couch 107 to a predetermined location with respect to bore 103. Motion controls 102 also enable a user to manually position couch 107 to a predetermined location.

Figure 2:
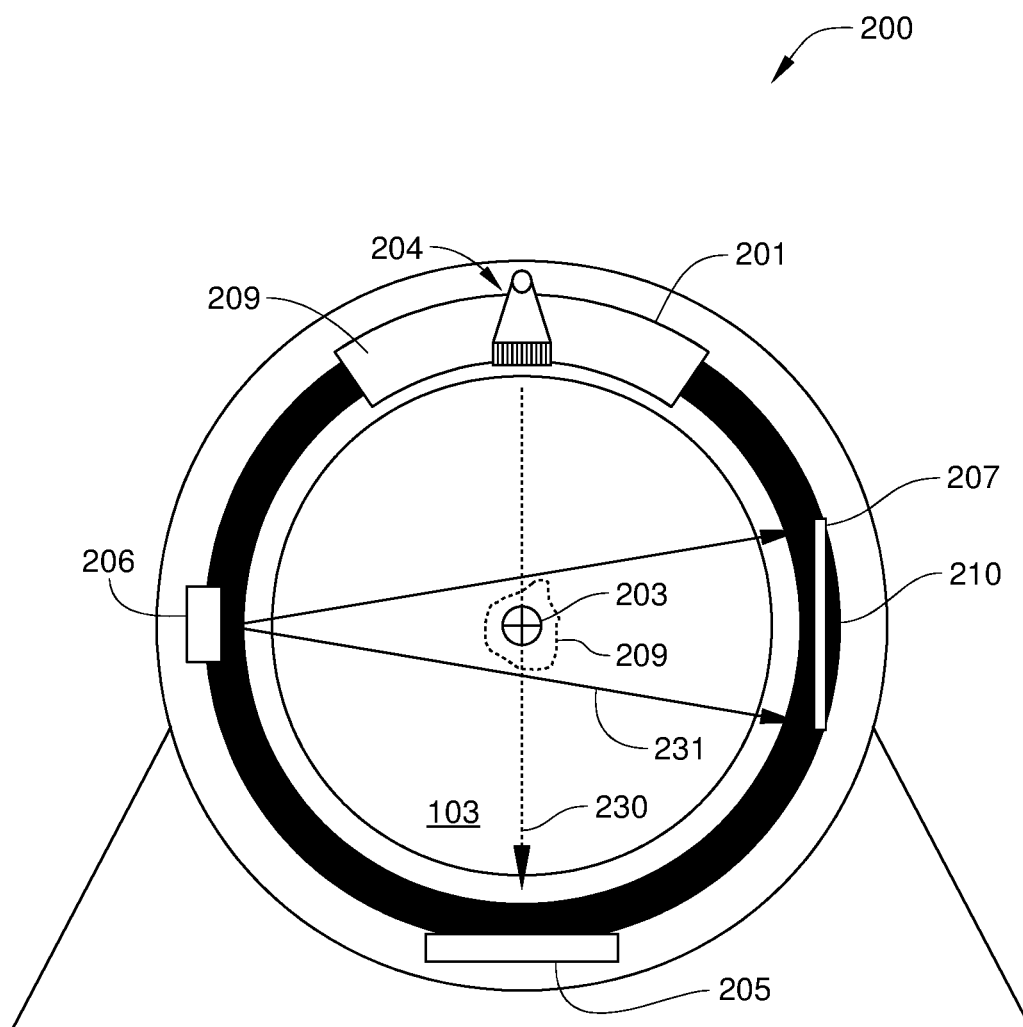
FIG. 2 schematically illustrates a drive stand and gantry of the radiation therapy system of FIG. 1, according to various embodiments.

FIG. 2 schematically illustrates a drive stand 200 and gantry 210 of RT system 100, according to various embodiments. Covers, base positioning assembly 105, couch 107, and other components of RT system 100 are omitted in FIG. 2 for clarity. Drive stand 200 is a fixed support structure for components of RT treatment system 110, including gantry 210 and a drive system 201 for rotatably moving gantry 210. Drive stand 200 rests on and/or is fixed to a support surface that is external to RT treatment system 110, such as a floor of an RT treatment facility. Gantry 210 is rotationally coupled to drive stand 200 and is a support structure on which various components of RT system 100 are mounted, including a linear accelerator (LINAC) 204, an MV electronic portal imaging device (EPID) 205, an imaging X-ray source 206, and an X-ray imager 207. During operation of RT treatment system 110, gantry 220 rotates about bore 103 when actuated by drive system 201.

Drive system 201 rotationally actuates gantry 210. In some embodiments, drive system 201 includes a linear motor that can be fixed to drive stand 200 and interacts with a magnetic track (not shown) mounted on gantry 210. In other embodiments, drive system 201 includes another suitable drive mechanism for precisely rotating gantry 210 about bore 201. LINAC 204 generates an MV treatment beam 230 of high energy X-rays (or in some embodiments electrons, protons, and/or other heavy charged particles, ultra-high dose rate X-rays (e.g., for FLASH radiotherapy) or microbeams for microbeam radiation therapy) and EPID 205 is configured to acquire X-ray images with treatment beam 230. Imaging X-ray source 206 is configured to direct a conical beam of X-rays, referred to herein as imaging X-rays 231, through an isocenter 203 of RT system 100 to X-ray imager 207, and isocenter 203 typically corresponds to the location of a target volume 209 to be treated. In the embodiment illustrated in FIG. 2, X-ray imager 207 is depicted as a planar device, whereas in other embodiments, X-ray imager 207 can have a curved configuration.

X-ray imager 207 receives imaging X-rays 231 and generates suitable projection images therefrom. According to certain embodiments, such projection images can then be employed to construct or update portions of imaging data for a digital volume that corresponds to a three-dimensional (3D) region that includes target volume 209. That is, a 3D image of such a 3D region is reconstructed from the projection images. In some embodiments, cone-beam computed tomography (CBCT) and/or digital tomosynthesis (DTS) can be used to process the projection images generated by X-ray imager 207. CBCT is typically employed to acquire projection images over a relatively long acquisition arc, for example over a rotation of 180° or more of gantry 210. As a result, a high-quality 3D reconstruction of the imaged volume can be generated. CBCT is often employed at the beginning of a radiation therapy session to generate a set-up 3D reconstruction. For example, CBCT may be employed immediately prior to application of treatment beam 230 to generate a 3D reconstruction confirming that target volume 209 has not moved or changed shape. Alternatively, or additionally, in some embodiments, partial-data reconstruction is performed by RT system 100 during portions of an IGRT or IMRT process in which partial image data is employed to generate a 3D reconstruction of target volume 209. For example, as treatment beam 230 is directed to isocenter 203 while gantry 210 rotates through a treatment arc, DTS image acquisitions can be performed to generate image data for target volume 209. Because DTS image acquisition is performed over a relatively short acquisition arc, for example between about 10° and 60°, near real-time feedback for the shape and position of target volume 209 can be provided by DTS imaging during the IGRT process.

In the embodiment illustrated in FIG. 2, RT system 100 includes a single X-ray imager and a single corresponding imaging X-ray source. In other embodiments, RT system 100 can include two or more X-ray imagers, each with a corresponding imaging X-ray source. One such embodiment is illustrated in FIG. 3.

Figure 3:
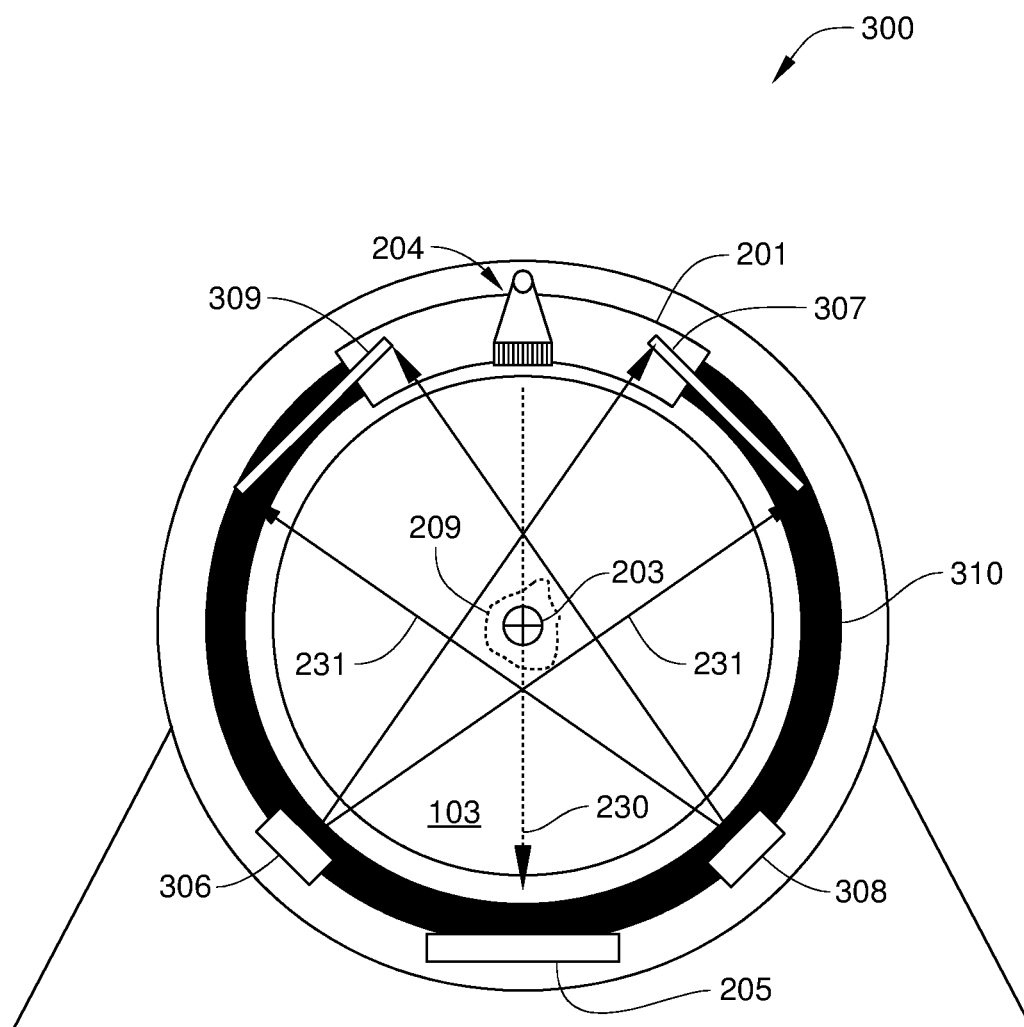
FIG. 3 schematically illustrates a drive stand and a gantry of the radiation therapy system of FIG. 1, according to various embodiments.

FIG. 3 schematically illustrates a drive stand 300 and gantry 310 of RT system 100, according to various embodiments. Drive stand 300 and gantry 310 are substantially similar in configuration to drive stand 200 and gantry 200 in FIG. 2, except that the components of RT system 100 that are mounted on gantry 310 include a first imaging X-ray source 306, a first X-ray imager 307, a second imaging X-ray source 308, and a second X-ray imager 309. In such embodiments, the inclusion of multiple X-ray imagers in RT system 100 facilitates the generation of projection images (for reconstructing the target volume) over a shorter image acquisition arc. For instance, when RT system 100 includes two X-ray imagers and corresponding X-ray sources, an image acquisition arc for acquiring projection images of a certain image quality can be approximately half that for acquiring projection images of a similar image quality with a single X-ray imager and X-ray source.

The projection images generated by X-ray imager 207 (or by first x-ray imager 307 and second X-ray imager 309) are used to construct imaging data for a digital volume of patient anatomy within a 3D region that includes the target volume. Alternatively or additionally, such projection images can be used to update portions of an existing imaging data for the digital volume corresponding to the 3D region. One embodiment of such a digital volume is described below in conjunction with FIG. 4.

Figure 4:
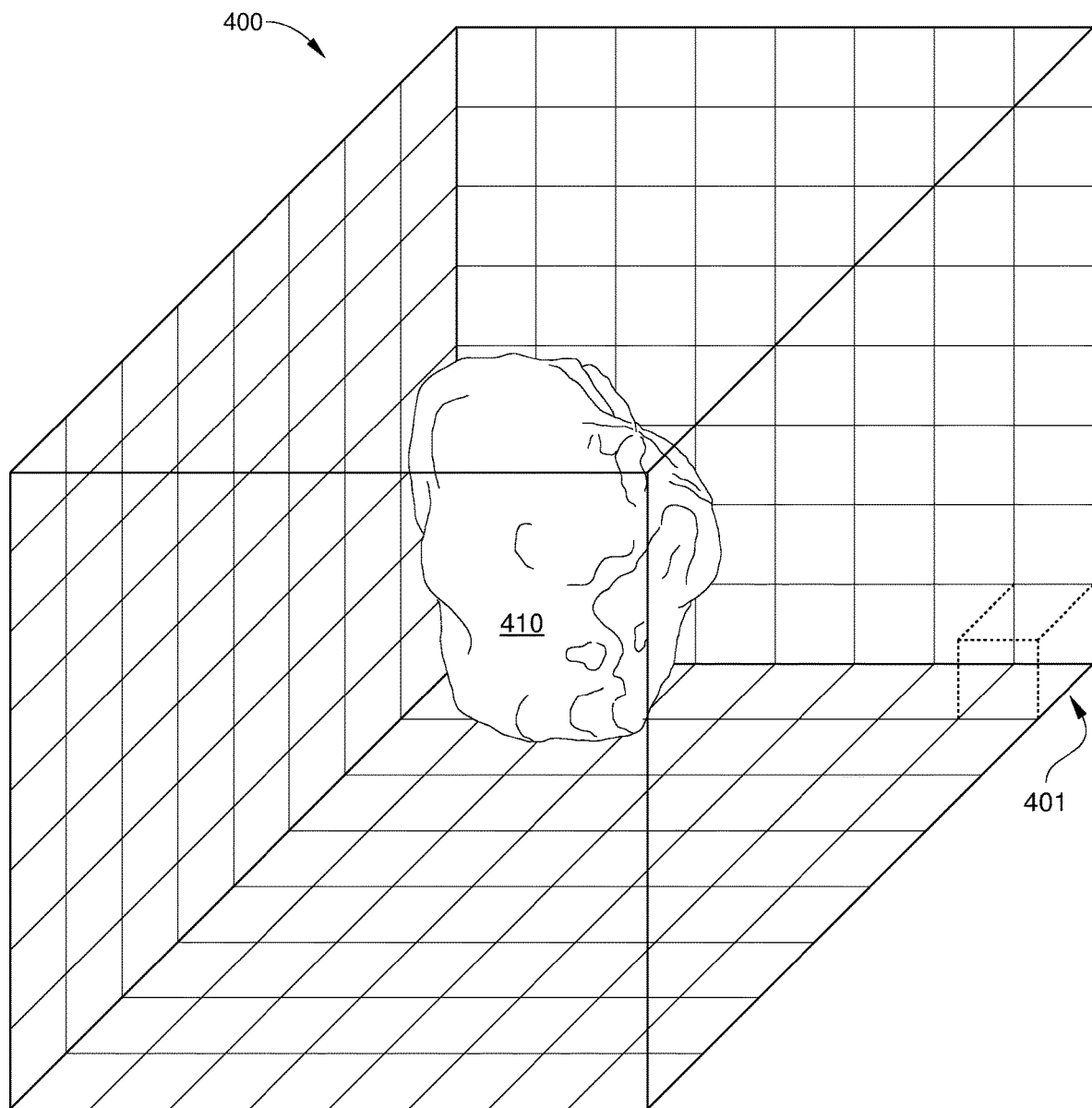
FIG. 4 schematically illustrates a digital volume that is constructed based on projection images generated by one or more X-ray images included in the radiation therapy system of FIG. 1, according to various embodiments.

FIG. 4 schematically illustrates a digital volume 400 that is constructed based on projection images generated by one or more X-ray imagers included in RT system 100, according to various embodiments. For example, in some embodiments, the projection images can be generated by a single X-ray imager, such as X-ray imager 207, and in other embodiments the projection images can be generated by multiple X-ray imagers, such as first x-ray imager 307 and second X-ray imager 309.

Digital volume 400 includes a plurality of voxels 401 (dashed lines) of anatomical image data, where each voxel 401 corresponds to a different location within digital volume 400. For clarity, only a single voxel 401 is shown in FIG. 4. Digital volume 400 corresponds to a 3D region that includes target volume 410. In FIG. 4, digital volume 400 is depicted as an 8×8×8 voxel cube, but in practice, digital volume 400 generally includes many more voxels, for example orders of magnitude more than are shown in FIG. 4.

For purposes of discussion, target volume 410 can refer to the gross tumor volume (GTV), clinical target volume (CTV), or the planning target volume (PTV) for a particular treatment. The GTV depicts the position and extent of the gross tumor, for example what can be seen or imaged; the CTV includes the GTV and an additional margin for subclinical disease spread, which is generally not imageable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by X-ray imaging of digital volume 400.

According to various embodiments described below, image information associated with each voxel 401 of digital volume 400 is constructed via projection images generated by the single or multiple X-ray imagers via a CBCT process. For example, such a CBCT process can be employed immediately prior to delivering treatment beam 230 to target volume 410, so that the location and shape of target volume 410 can be confirmed before treatment begins. In addition, in some embodiments, image information associated with some or all of voxels 401 of digital volume 400 is updated via projection images generated by the single or multiple X-ray imagers via a DTS process. For example, such a DTS process can be employed after a portion of a planned treatment has begun and before the planned treatment has completed. In this way, the location and shape of target volume 410 can be confirmed while the treatment is underway.

CBCT Image Acquisition with Metal Object Present

Figure 5:
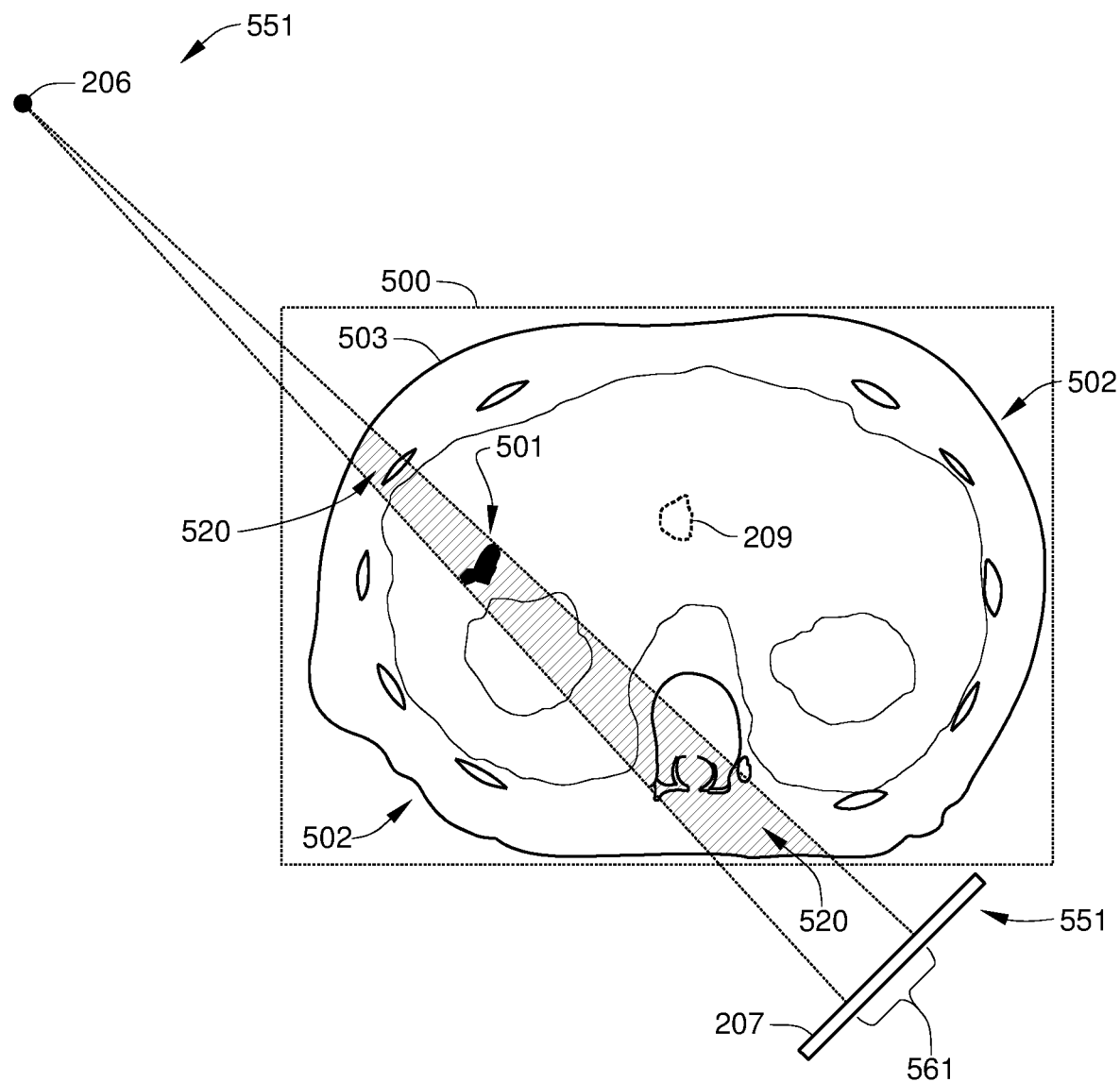
FIG. 5 schematically illustrates the effect of a metal object on the imaging of a region of patient anatomy, according to an embodiment.

FIG. 5 schematically illustrates the effect of a metal object 501 on the imaging of a region 502 of patient anatomy, according to an embodiment. Region 502 can be any technically feasible portion of patient anatomy, including the head, chest, abdomen, and the like. In the embodiment illustrated in FIG. 5, CBCT image acquisition is performed via imaging X-ray source 206 and X-ray imager 207 over a digital volume 500 that includes target volume 209 and extends to an edge surface 503 of region 502. In other embodiments, multiple X-ray sources and X-ray imagers can be employed. Alternatively or additionally, in some embodiments, digital volume 500 does not include all of edge surface 503, or does not include any portion of edge surface 503.

FIG. 5 shows a 2D projection being acquired with imaging X-ray source 206 and X-ray imager 207 disposed at a one particular image acquisition position 551. In practice, CBCT image acquisition is performed at a plurality of image acquisition positions around region 502 to enable generation of a digital reconstruction of digital volume 500. Thus, while disposed image acquisition position 551, imaging X-ray source 206 and X-ray imager 207 acquire one of a set of multiple CBCT 2D projection images that together are employed to reconstruct region 502. Further, in FIG. 5, X-ray imager 207 is viewed edge-on, and therefore is depicted as a one-dimensional imaging structure. In reality, X-ray imager 207 is typically configured to generate 2D projection images at each of a plurality of image acquisition locations.

Metal object 501 can be any metallic object that appears in an X-ray image of region 502 (and/or in a digital reconstruction of region 502). For example, in some instances, metal object 501 is one of a fiducial marker, a surgical staple or other medical device, a dental component, an orthopedic component, and/or the like.

As shown, when X-ray imager 207 is in first image acquisition position 551, metal object 501 appears in pixels 561 of X-ray imager 207. Thus, in the 2D projection acquired at first image acquisition position 551, pixels 561 are associated with metal object 501. It is noted that metal object 501 can significantly contribute to visual artifacts and/or other inconsistencies when the 2D projection images acquired by X-ray imager 207 are employed to reconstruct a 3D volume of region 502. For example, the presence of high contrast of metal object 501 modulates the X-ray spectrum in a way that is not modelled by typical reconstruction algorithms (which generally assume that all scanned objects have a radiodensity that is approximately that of water). Consequently, visual artifacts can result. Further, in instances in which high contrast metal object 501 is relatively large, other information in blocked portions 520 (cross-hatched) of region 502 can be obscured, where blocked portions 520 are the portions of region 502 that are imaged by the same pixels of a 2D projection of region 502 as metal object 501.

Reduction of Visual Artifacts Due to Metal Objects

According to various embodiments described below, visual artifacts (not shown) that occur in a reconstructed volume of region 502 due to the presence of metal object 501 are reduced or removed in a computer-implemented process for imaging a subject region, such as a region of patient anatomy. One such embodiment is described below in conjunction with FIG. 6.

Figure 6:
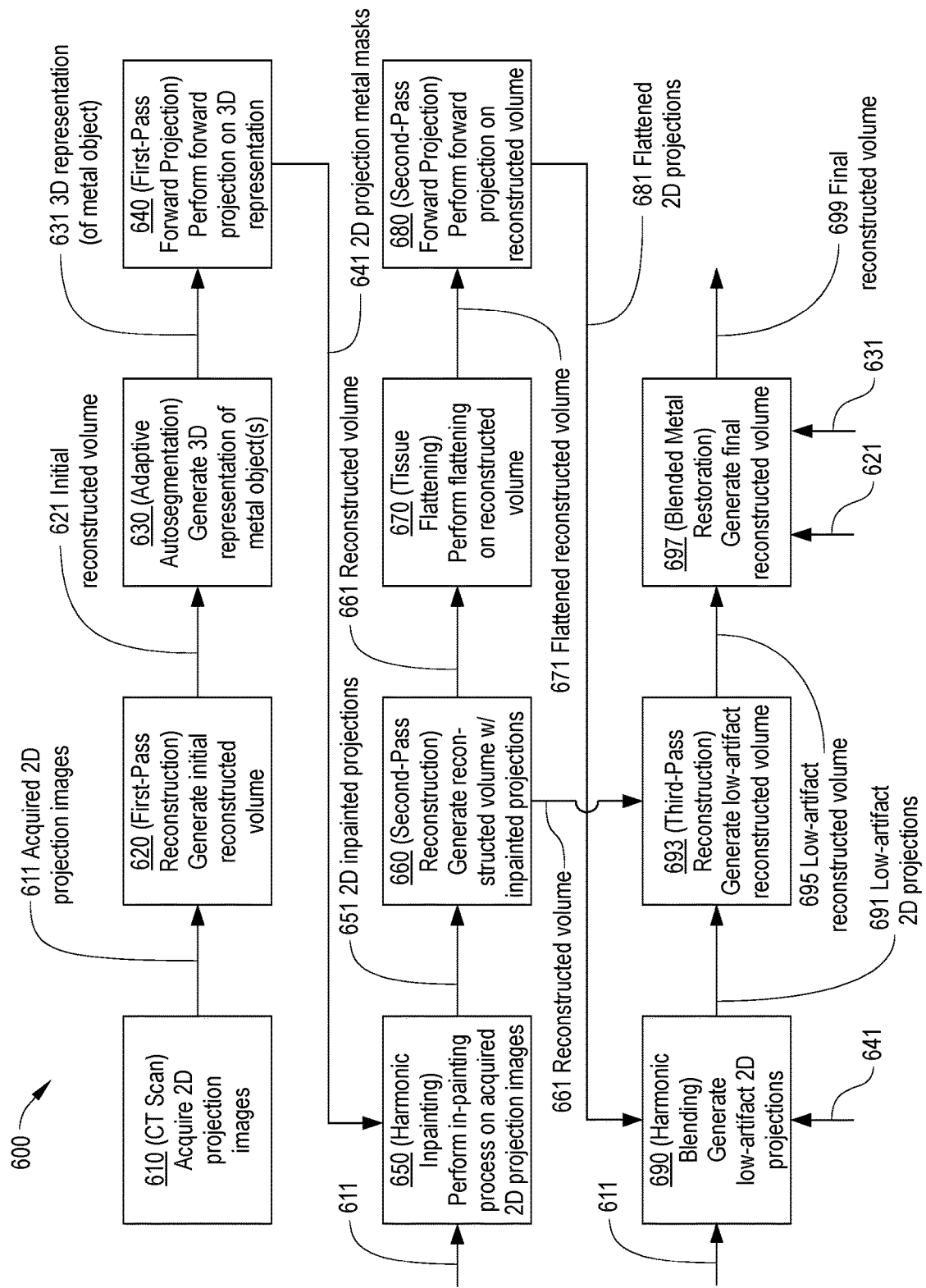
FIG. 6 sets forth a flowchart of a computer-implemented process for imaging a region of patient anatomy, according to one or more embodiments.

FIG. 6 sets forth a flowchart of a computer-implemented process 600 for imaging a region of patient anatomy, according to one or more embodiments. Computer-implemented process 600 can be implemented as an imaging-only process, or in conjunction with radiation therapy, such as IGRT, stereotactic radiosurgery (SRS), and the like. Further, computer-implemented process 600 may be performed over a single rotational arc of a gantry of a radiation therapy or imaging system, over a fraction of a rotational arc, or over multiple rotational arcs. Computer-implemented process 600 may include one or more operations, functions, or actions as illustrated by one or more of blocks 610-697. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although computer-implemented process 600 is described in conjunction with the X-ray imaging system described herein as part of radiation therapy system 100 and FIGS. 1-5, persons skilled in the art will understand that any suitably configured X-ray imaging system is within the scope of the present embodiments.

In step 610, a CT or CBCT scan is performed. For example, in some embodiments, the X-ray imaging system of radiation therapy system 100 acquires a set of acquired 2D projection images 611 of region 502, which includes target volume 209 and metal object 501. Thus, region 502 includes at least one metallic object (e.g., metal object 501).

In step 620, a first-pass reconstruction process is performed. For example, in some embodiments, the X-ray imaging system generates an initial reconstructed volume 621 (first reconstructed volume) of region 502 based on acquired 2D projection images 611. Initial reconstructed volume 621 is a 3D volumetric data set of region 502. In some embodiments, a Feldkamp, Davis and Kress (FDK) reconstruction algorithm is employed to generate an initial reconstructed volume 621. In other embodiments, an algebraic reconstruction technique (ART) or other iterative reconstruction technique is employed to generate initial reconstructed volume 621, and in yet other embodiments, any other suitable reconstruction algorithm is employed. It is noted that initial reconstructed volume 621 generally includes visual artifacts due to the presence of metal object 501 in region 502.

In step 630, a novel adaptive autosegmentation process is performed on metal objects disposed within initial reconstructed volume 621 to generate a 3D representation of the metal objects. For example, in some embodiments, the X-ray imaging system performs an autosegmentation of metal object 501 to generate a 3D representation 631 of metal object 501 disposed within region 502. Generally, the adaptive autosegmentation process of step 630 is performed automatically on initial reconstructed volume 621, and user input is not required to perform an adjustment of segmentation parameter values. 3D representation 631 includes 3D location information of metal object 501. In some embodiments, in the novel adaptive autosegmentation process of step 630, patient anatomy in region 502 is identified and classified, and the type of metal present in region 502 is determined. Based on the patient anatomy and type or volume of metal, suitable segmentation parameter values (such as thresholding values and dilation radii) are determined and employed to generate 3D representation 631 of metal object 501, sometimes referred to as a 3D metal object mask. One embodiment of the novel adaptive autosegmentation process is described below in conjunction with FIG. 7. Alternatively, in some embodiments, any suitable segmentation algorithm or software application configured to generate 3D location information of metal object 501 can be employed in step 630, such as an algorithm that depends on user inputs indicating patient anatomy and/or a type of metal associated with metal object(s) 501.

In step 640, a first-pass forward projection process is performed. For example, in some embodiments, the X-ray imaging system performs a forward projection process on 3D representation 631 to generate a set of 2D projection metal masks 641. Each 2D projection metal mask 641 in the set of 2D projection metal masks 641 includes location information indicating pixels that are blocked by metal object 501 during the forward projection process of step 640. In step 640, each 2D projection metal mask 641 generated is selected to correspond to a different acquired 2D projection image 611 included in the set of acquired 2D projection images 611 acquired in step 610. That is, for each 2D projection metal mask 641 generated in step 640, the forward projection process is performed using the same projection angle used to acquire one of acquired 2D projection images 611. Thus, each 2D projection metal mask 641 matches a corresponding acquired 2D projection image 611. For example, in some embodiments, each 2D projection metal mask 641 can be combined with a corresponding acquired 2D projection image 611 in the harmonic in-painting process of step 650.

In some embodiments, in step 640 an additional thresholding process is applied to each 2D projection metal mask 641. The thresholding process normalizes the pixels of a particular 2D projection metal mask 641 to be in the interval [0,1], where 1 corresponds to the contrast structure and 0 to the rest of region 502 (and therefore not a part of 2D projection metal mask 641).

In step 650, a novel harmonic inpainting process is performed. For example, in some embodiments, the X-ray imaging system performs a harmonic in-painting process on acquired 2D projection images 611 to generate a set of 2D inpainted projections 651 of region 502. Specifically, each 2D inpainted projection 651 is generated by modifying a portion of an acquired 2D projection image 611. For the acquired 2D projection image 611, visual information (e.g., a pixel value) associated with metal object 501 is removed, based on location information included in the corresponding 2D projection metal mask 641. For example, in such an embodiment, the 2D projection metal mask 641 indicates pixels that are associated with metal object 501. Pixel values for these pixels are removed from the particular acquired 2D projection image 611 and are replaced with lower-contrast pixel values via an inpainting process. One embodiment of the harmonic inpainting process is described below in conjunction with FIG. 8. Alternatively, in some embodiments, any suitable inpainting algorithm can be employed in step 650 to generate the set of 2D inpainted projections 651.

In step 660, a second-pass reconstruction process is performed. For example, in some embodiments, the X-ray imaging system generates a reconstructed volume 661 (second reconstructed volume) of region 502 based on the 2D inpainted projections 651 generated in step 650. In some embodiments, ART is employed to generate reconstructed volume 661, and in other embodiments, an FDK reconstruction algorithm or other reconstruction algorithm may be employed to generate reconstructed volume 661. Reconstructed volume 661 is similar to initial reconstructed volume 621, except that metal object 501 has been removed.

In step 670, a tissue-flattening process is performed. For example, in some embodiments, the X-ray imaging system performs a flattening process on reconstructed volume 661 to generate a flattened reconstructed volume 671. Generally, flattened reconstructed volume 671 contains the original information about bones while information related to soft tissue is replaced with a single value. Thus, in a subsequent step, a blending process restores bone information, while for soft tissue the blending process acts as the inpainting performed in the first-pass reconstruction if step 620. In some embodiments, a simple thresholding method is employed in step 670 to generate flattened reconstructed volume 671, and in other embodiments, a filtering and/or convolutional neural network may also be employed in step 670 to generate flattened reconstructed volume 671.

In step 680, a second-pass forward projection process is performed. For example, in some embodiments, the X-ray imaging system performs a forward projection process on flattened reconstructed volume 671 to generate a set of flattened 2D projections 681. It is noted that in each flattened 2D projection 681, pixels that are visually blocked by metal object 501 (i.e., pixels that are indicated by location information in a 2D projection metal mask to be associated with metal object 501) have pixel values that do not include a contribution from metal object 501. Instead, in each flattened 2D projection 681, the pixel values for pixels that are visually blocked by metal object 501 are based on flattened reconstructed volume 671, which includes bone information for region 502.

In step 680, each flattened 2D projection 681 generated is selected to correspond to a different acquired 2D projection image 611 included in the set of acquired 2D projection images 611 acquired in step 610. That is, for each flattened 2D projection 681 generated in step 680, the forward projection process is performed using the same projection angle used to acquire one of acquired 2D projection images 611. Thus, each flattened 2D projection 681 matches a corresponding acquired 2D projection image 611, and can be combined therewith subsequently, for example in the blending process of step 690.

In step 690, a novel harmonic blending process is performed. For example, in some embodiments, the X-ray imaging system generates a set of low-artifact 2D projections 691 of region 502 by modifying acquired 2D projection images 611 based on 2D projection metal masks 641 and flattened 2D projections 681. Specifically, location information from 2D projection metal masks 641 indicates certain pixels of acquired 2D projection images 611 that are to have image information (e.g., pixel values) replaced with image information from corresponding pixels of flattened 2D projections 681. It is noted that in general, the majority of pixels of low-artifact 2D projections 691 have the same pixel values and/or other image information as the corresponding pixels of acquired 2D projection images 611. However, the pixels of low-artifact 2D projections 691 that are indicated to be blocked by or associated with metal object 501 include pixel values and/or other image information that are different from the corresponding pixels of acquired 2D projection images 611.

In some embodiments, a harmonic blending process is performed to minimize or otherwise reduce visual artifacts caused by replacing image information for groups of pixels in acquired 2D projection images 611 with pixel information from flattened 2D projections 681. For example, in an embodiment, acquired 2D projection images 611 form a set of projections $P_1 \ldots P_n$, flattened 2D projections 681 form a set of projections $F_1 \ldots F_n$, and 2D projection metal masks 641 form a set of masks $M_1 \ldots M_n$. In the embodiment, projections $F_1 \ldots F_n$ are combined with projections $P_1 \ldots P_n$ in the metal regions indicated by masks $M_1 \ldots M_n$. Specifically, the inpainting of such metal regions of projections $P_1 \ldots P_n$ is performed by element-wise division $P_i/F_i$ and after the inpainting, the new values for the metal regions are post-multiplied by values corresponding pixels from $F_i$. In the inpainting process, pixel values for mask-bordering pixels (pixels within projections $P_1 \ldots P_n$ that are adjacent to a mask-edge pixel of a metal region of masks $M_1 \ldots M_n$) are used as boundary conditions. Further, in the harmonic inpainting process, pixel values for mask-edge pixels are constrained to a certain pixel value based on the pixel value of an adjacent mask-bordering pixel. Specifically, for each mask-edge pixel, the pixel value is constrained so that a change in slope of pixel value associated with the mask-edge pixel is equal to a change in slope of pixel value associated with an adjacent mask-bordering pixel. In some embodiments, a harmonic function is employed to enforce such a constraint on the pixel values of the mask-edge pixel. In some embodiments, the harmonic inpainting process for generating low-artifact 2D projections 691 is similar to the harmonic inpainting process for generating 2D inpainted projections 651, which is described in greater detail below in conjunction with FIG. 7.

In step 693, a third-pass reconstruction process is performed. For example, in some embodiments, the X-ray imaging system executes a reconstruction algorithm using the set of low-artifact 2D projections 691 of region 502 to generate a low-artifact reconstructed volume 695 (third reconstructed volume) of region 502. Thus, the X-ray imaging system generates low-artifact reconstructed volume 695 of region 502 based on the low-artifact 2D projections 691 generated in step 690. In some embodiments, an FDK reconstruction algorithm is employed to generate low-artifact reconstructed volume 695. In other embodiments, an ART algorithm may be employed to generate low-artifact reconstructed volume 695. In other embodiments, a penalized-likelihood (PL) reconstruction algorithm is employed to generate low-artifact reconstructed volume 695. Alternatively, any other suitable reconstruction algorithm can be employed in step 690. Low-artifact reconstructed volume 695 is similar to initial reconstructed volume 621, except that metal object 501 has been removed and artifacts caused by the presence of metal object 501 have been removed and/or reduced in visual prominence.

In step 697, a blended metal restoration process is performed. For example, in some embodiments, the X-ray imaging system generates a final reconstructed volume 699 (fourth reconstructed volume) of region 502. In step 697, the X-ray imaging system blends low-artifact reconstructed volume 695 with image information (e.g., pixel values) from initial reconstructed volume 621 and from 3D representation 631 of metal object 501. Thus, final reconstructed volume 699 is generated by restoring metal object information to low-artifact reconstructed volume 695.

In some embodiments, the blended metal restoration process of step 697 includes operations that create a smooth transition between metal and non-metal parts within final reconstructed volume 699. In such embodiments, edge voxels of metal object 501 are not represented as voxels that have values equal to 100% of the radiographic density of voxels within metal object 501. Instead, each edge voxel of metal object 501 in final reconstructed volume 699 has a value that is based on a combination of an image value from the corresponding voxel of initial reconstructed volume 621, an image value from the corresponding voxel of low-artifact reconstructed volume 695, and information from the corresponding voxel of metal mask 3D representation 631. Specifically, the blended metal restoration process of step 697 includes a blending of three inputs: initial reconstructed volume 621, low-artifact reconstructed volume 695, and a non-binary mask W that is based on metal mask 3D representation 631.

Non-binary mask W is based on the metal mask 3D representation 631, but differs in some respects. Metal mask 3D representation 631 is a binary mask that indicates whether or not a particular voxel location in low-artifact reconstructed volume 695 should be considered a portion of metal object 501. Thus, metal mask 3D representation 631 applies a binary decision to each voxel of low-artifact reconstructed volume 695. For example, $M_{voxel\ i}=1$ when voxel i of a mask M is considered a portion of metal object 501 and $W_{voxel\ i}=0$ when voxel i of a mask M is considered not a portion of metal object 501. By contrast, non-binary mask W differs from metal mask 3D representation 631 in that values for non-binary mask W can vary between 0 and 1 for some or all edge voxels of metal object 501.

In some embodiments, a value $W_{vox}$ for each voxel of non-binary mask W is determined based on a value $V_{vox}$ for a corresponding voxel of initial reconstructed volume 621. In some embodiments, when $V_{vox}$ is greater than a metal thresholding value $t_{metal}$ (such as the metal thresholding value employed to generate metal mask 3D representation 631 in step 630), $W_{vox}=1$; when $V_{vox}$ is less than a tissue thresholding value $t_{tissue}$ (for example 300 HU), $W_{vox}=0$; and when $V_{vox}$ is between metal thresholding value $t_{metal}$ and tissue thresholding value $t_{tissue}$, Wvox=w, where w is a value between 0 and 1. In such embodiments, w may be based on a value for the corresponding voxel of initial reconstructed volume 621, metal thresholding value $t_{metal}$, and tissue thresholding value $t_{tissue}$. For example, in one such embodiment, when $V_{vox}$ is between metal thresholding value $t_{metal}$ and tissue thresholding value $t_{tissue}$, $w=(V_{vox}-t_{tissue})/t_{metal}-t_{tissue}$). Thus, in such an embodiment, a linear interpolation is applied in determining a value for w. In other embodiments, when $V_{vox}$ is between metal thresholding value and tissue thresholding value $t_{tissue}$, w may be calculated based on any other suitable algorithm that includes metal thresholding value $t_{metal}$ and tissue thresholding value $t_{tissue}$, or some other measure of how much of the volume of $V_{vox}$ corresponds to a metal material.

In some embodiments, the blended metal restoration process of step 697 determines pixel values of final reconstructed volume 699 using a weighted alpha-blending of the three inputs: initial reconstructed volume 621, low-artifact reconstructed volume 695, and non-binary mask W. Further, in one such embodiment, a maximum operator is applied to voxel values of initial reconstructed volume 621 and low-artifact reconstructed volume 695. In such an embodiment, a value $V_{FINAL}$ for a voxel of final reconstructed volume 699 is determined based on Equation 1:

$$V_{FINAL}=(1-w)*V_{696}+w*\max\{V_{695}, V_{621}\} \quad (1)$$

where $V_{695}$ is the value of the corresponding voxel of low-artifact reconstructed volume 695 and $V_{621}$ is the value of the corresponding voxel of initial reconstructed volume 621. In such embodiments, the application of the maximum operator to $V_{695}$ and $V_{621}$ restores a smooth transition between soft tissue and the metal objects in final reconstructed volume 695.

Adaptive Autosegmentation of Metal Objects

Appropriate extraction of a projection metal mask (also referred to as a metal trace) is important in CBCT reconstruction to ensure the image quality of a final reconstructed volume of a region of patient anatomy. When the metal trace is underestimated, metal-related artifacts are not completely suppressed. On the other hand, overestimation of a metal trace can lead to excessive inpainting, which results in redundant suppression of important, non-metal image information in the final reconstructed volume. In such situations, images generated from the final reconstructed volume can suffer from an unnecessary loss of detail, which is highly undesirable in multiple applications.

In the adaptive autosegmentation process of step 630, an autosegmentation is performed on metal object(s) 501 disposed within initial reconstructed volume 621 to generate a metal trace (e.g., 3D representation 631) of metal objects(s) 501. Generally, autosegmentation of metal objects from a reconstructed volume depends on several segmentation parameters, including a radiographic density threshold (referred to herein as a "thresholding parameter") and a dilation diameter (for improving mask quality at the mask boundary). Fully automated segmentation processes have had poor performance due to the dependence of such processes on correct values for such parameters. For example, an autosegmentation process tuned to detecting a hip prostheses can fail when applied to the detection of dental metals, due to the much smaller size of dental metal objects and the different structure of the environment surrounding such metal objects. Consequently, for a successful autosegmentation process, user inputs are generally required that indicate the anatomical region associated with scanned image data and the specific type of metal objects disposed within the anatomical region.

According to various embodiments, an adaptive autosegmentation process, such as the adaptive autosegmentation process of step 630, is performed automatically on a reconstructed volume, and user inputs are not required to perform an adjustment of segmentation parameter values. In such embodiments, a region of patient anatomy associated with the reconstructed volume is identified and classified, and the type of metal present in the reconstructed volume is determined. Based on the region of patient anatomy and the type of metal, accurate segmentation parameter values are determined and employed to generate a 3D metal object mask for the reconstructed volume, such as 3D representation 631 of metal object 501. One such embodiment is described below in conjunction with FIG. 7.

Figure 7:
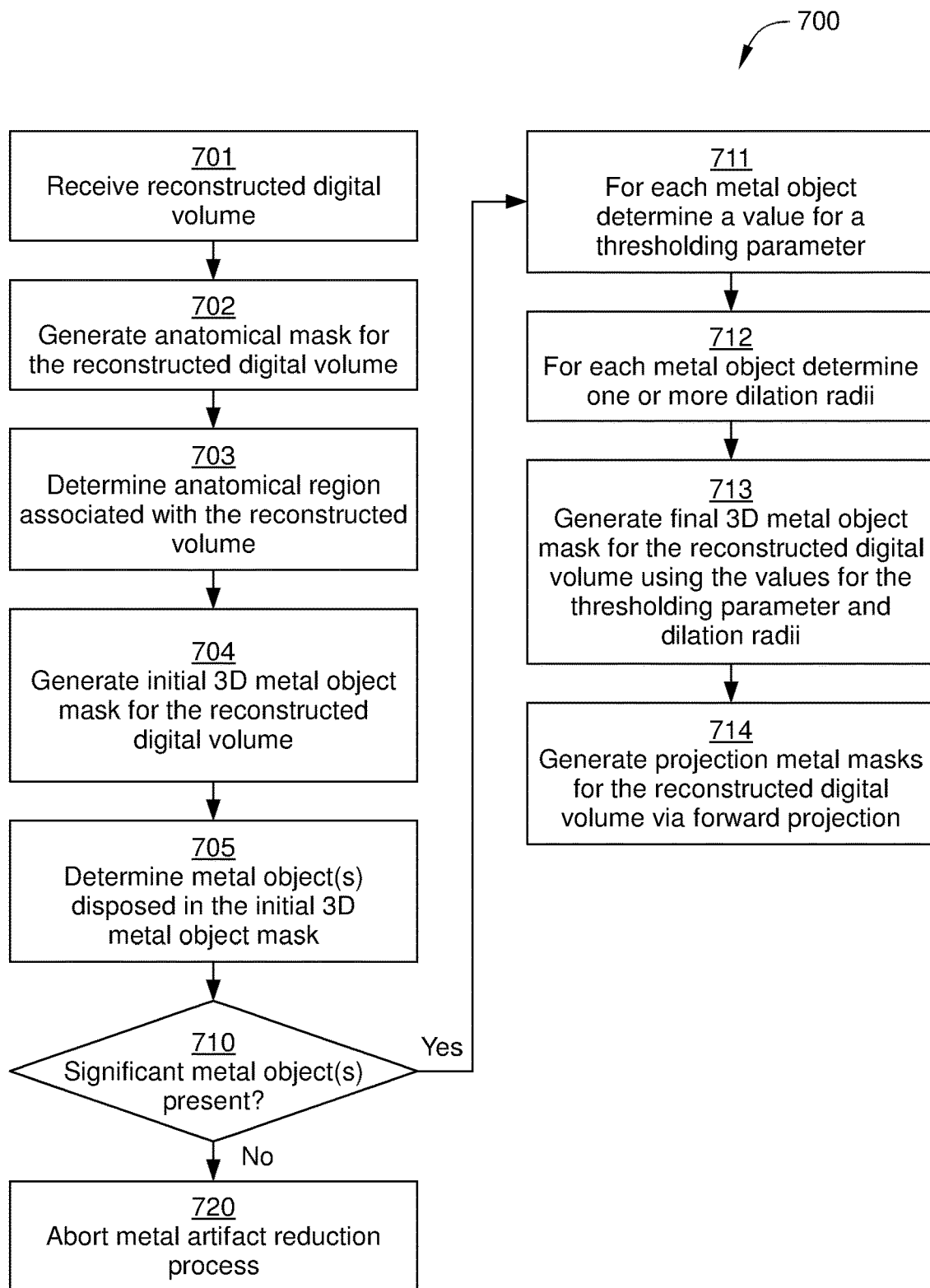
FIG. 7 sets forth a flowchart of a computer-implemented process for segmenting a reconstructed volume of a region of patient anatomy, according to one or more embodiments.

FIG. 7 sets forth a flowchart of a computer-implemented process 700 for segmenting a reconstructed volume of a region of patient anatomy, according to one or more embodiments. Computer-implemented process 700 can be implemented as part of an imaging-only process, or in conjunction with radiation therapy, such as IGRT, stereotactic radiosurgery (SRS), and the like. Computer-implemented process 700 may include one or more operations, functions, or actions as illustrated by one or more of blocks 701-720. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although computer-implemented process 700 is described in conjunction with the X-ray imaging system described herein as part of radiation therapy system 100 and FIGS. 1-6, persons skilled in the art will understand that any suitably configured X-ray imaging system is within the scope of the present embodiments.

In step 701, the X-ray imaging system of radiation therapy system 100 receives a reconstructed digital volume, such as initial reconstructed volume 621.

In step 702, the X-ray imaging system generates an anatomical mask for reconstructed volume 621. In some embodiments, the anatomical mask is configured to include locations of initial reconstructed volume 621 based on an anatomical threshold value. For example, in some embodiments, the X-ray imaging system performs a thresholding operation on initial reconstructed volume 621 using an anatomical threshold value. In such embodiments, the anatomical threshold value is selected so that voxels associated with patent anatomy are included in the anatomical mask and voxels associated with air or other matter external to the patient anatomy are excluded from the anatomical mask. In some embodiments, the anatomical threshold value is associated with a material having a radiodensity that is greater than that of air and/or less than that of water.

In step 703, the X-ray imaging system determines the anatomical region associated with initial reconstructed volume 621. Examples of anatomical regions that can be determined via the anatomical mask include the head and/or neck, the pelvis, the abdomen, portions of a limb, and/or the like. The anatomical mask provides the shape and size in three dimensions of the anatomical region. Thus, any technically feasible approach can be employed to determine the specific anatomical region that is associated with initial reconstructed volume 621. For example, in some embodiments, a suitably trained machine-learning algorithm can be employed for classifying the specific anatomical region that is associated with initial reconstructed volume 621. Because the number of different anatomical regions that can possibly be associated with initial reconstructed volume 621 is limited, in some embodiments, a simplified geometrical analysis is employed to classify the specific anatomical region that is associated with initial reconstructed volume 621.

In embodiments in which a geometrical analysis is employed, the geometrical analysis includes determining whether the anatomical region is a head region or a body region, based on the anatomical mask. In such embodiments, a minimum lateral width of the anatomical mask can indicate whether the anatomical region is a head region or a body region. For example, in normal instances, a minimum lateral width of patient anatomy represented by the anatomical mask above 25 cm indicates a body scan and a minimum lateral width of patient anatomy represented by the anatomical mask below 20 cm indicates a head scan. Consequently, in some embodiments, a maximum lateral width for each slice in the anatomical mask that has a non-zero width is measured (for example, in voxels). A minimum lateral width of these maximum lateral width measurements is then determined to be the minimum lateral width of the anatomical mask. Comparison of such a minimum lateral width to a maximum head width threshold value and/or to a minimum body width threshold indicates whether the anatomical region is a head region or a body region. Additionally or alternatively, in some embodiments, one or more additional geometric analyses can be applied to certain dimensions of the anatomical mask to determine other anatomical regions, such as an upper arm, lower arm, thigh, etc.

In step 704, the X-ray imaging system generates an initial 3D metal object mask $M_{init}$ for initial reconstructed volume 621. For example, in some embodiments, the X-ray imaging system generates initial 3D metal object mask $M_{init}$ by performing an image thresholding operation on initial reconstructed volume 621, based on an initial metal threshold value $t_{init}$. In some embodiments, initial metal threshold value $t_{init}$ is selected to ensure that all metal objects disposed within initial reconstructed volume 621 are detected. For example, in some embodiments, $t_{init}$ is a value between about 1200 HU and 1800 HU. Further, in some embodiments, to ensure that only metal objects inside patient anatomy are included in initial 3D metal object mask $M_{init}$, initial 3D metal object mask $M_{init}$ is multiplied by the anatomical mask (which can be a binary mask of values 1 or 0). Thus, in such embodiments, metal objects outside patient anatomy are eliminated by pixel values associated with such metal objects being multiplied by 0.

In step 705, the X-ray imaging system determines whether metal objects, such as tooth fillings, fiducials, or orthopedic prostheses, are disposed within initial reconstructed volume 621. Generally, the X-ray imaging system determines metal objects disposed within initial reconstructed volume 621 using voxels indicated by initial 3D metal object mask $M_{init}$. In some embodiments, the X-ray imaging system further determines metal objects disposed within initial reconstructed volume 621 by detecting one or more connected components contained within initial 3D metal object mask $M_{init}$. In such embodiments, each connected component includes a set of connected, adjacent, and/or contiguous voxels within initial reconstructed volume 621. In such embodiments, any suitable algorithm can be employed to determine connected components within initial 3D metal object mask $M_{init}$. For example, in some embodiments, a method of determining connected components is presented in: "Sequential Operations in Digital Picture Processing", A. Rosenfeld and J. Pfaltz. Journal of the ACM. Vol. 13, Issue 4, October 1966, Pg. 471-494.

In some embodiments, the X-ray imaging system can determine a size (or volume) $s_c$ and a mean radiographic density value (such as a mean HU value) $v_c$ for each connected component. In such embodiments, a vector of pairs ($[s_1,v_1], \ldots [s_n,v_n]$) can be generated to facilitate determining whether significant metal objects are disposed within initial reconstructed volume 621. In such embodiments, a metal classification of initial reconstructed volume 621 can be determined based on certain information included in and/or associated with the vector of pairs ($[s_1, v_1], \ldots [s_n,v_n]$). Examples of such information include a volume of a largest component of the one or more connected components, a cumulative volume of a set of the one or more connected components that are larger than a predetermined volume, and a radiographic density of at least one of the one or more connected components that are larger than a predetermined volume.

In step 710, the X-ray imaging system determines whether significant metal objects, such as metal objects of significant size, are disposed within initial reconstructed volume 621. For example, in some embodiments, the X-ray imaging system performs a classification operation in step 710 to determine whether significant metal objects are disposed within initial reconstructed volume 621. Examples of metal classifications that can be applied to initial reconstructed volume 621 include a metal-free anatomical region, a dental region, a fiducial-containing region (such as the abdomen), an orthopedic region, (such as the pelvic region), and/or the like.

In an example metal classification operation performed in step 710, the X-ray imaging system determines initial reconstructed volume 621 to be a metal-free anatomical region when the vector of pairs ($[s_1,v_1], \ldots [s_n,v_n]$) is empty, when a largest connected component in a head anatomical region has a volume of less than a first threshold value (e.g. 50 mm$^3$), and/or when no connected component with a volume of less than a second threshold value (e.g. 200 mm$^3$) has a mean radiographic density value $v_c$ above a third threshold value (e.g., 2000 HU). In addition, in the example metal classification operation, the X-ray imaging system determines initial reconstructed volume 621 to be a dental region when at least one connected component in a head anatomical region has a volume of at least the first threshold value (e.g. 50 mm$^3$). Further, in the example metal classification operation, the X-ray imaging system determines initial reconstructed volume 621 to be an orthopedic region when connected components in a body anatomical region have a cumulative volume of at least a fourth threshold value (e.g. 10000 mm$^3$). Further, in the example metal classification operation, the X-ray imaging system determines initial reconstructed volume 621 to be a fiducial-containing region when at least one small connected component (e.g., a connected component having a volume of less than the second threshold value) in a body anatomical region has a mean value of at least a fifth threshold value (e.g. 20000 HU).

In step 710, when the X-ray imaging system determines significant metal objects are disposed within initial reconstructed volume 621, method proceeds to step 711. When the X-ray imaging system determines significant metal objects are not disposed within initial reconstructed volume 621, method proceeds to step 720.

In step 711, for each metal object or connected component disposed within initial reconstructed volume 621, the X-ray imaging system determines a suitable value for a thresholding parameter. For example, in some embodiments, a dental threshold value $t_{dental}$ is selected for connected components associated with a dental region, such as 4000 HU; a fiducial threshold value $t_{fiducial}$ is selected for connected components associated with a fiducial-containing region, such as 2000 HU; and an orthopedic threshold value $t_{ortho}$ is selected for connected components associated with an orthopedic region, such as 1600 HU.

In step 712, for each metal object or connected component disposed within initial reconstructed volume 621, the X-ray imaging system determines a suitable value for a dilation radius. For example, in some embodiments, one or more dental dilation radii are selected for connected components associated with a dental region, such as an in-plane radius of 2 mm and an out-of-plane radius of 2 mm; one or more fiducial dilation radii are selected for connected components associated with a fiducial-containing region, such as an in-plane radius of 2 mm and an out-of-plane radius of 2 mm; and one or more orthopedic dilation radii are selected for connected components associated with an orthopedic region, such as an in-plane radius of 3 mm and an out-of-plane radius of 10 mm.

In step 713, the X-ray imaging system generates a final 3D metal object mask (e.g., 3D representation 631) for initial reconstructed volume 621 using the values determined in step 711 and 712 for the thresholding parameter and the dilation radii. Thus, in step 713, the X-ray imaging system performs an autosegmentation of initial reconstructed volume 621 using the values for the thresholding parameter and the dilation radii.

In step 714, the X-ray imaging system generates a set of projection metal masks (e.g., 2D projection metal masks 641) for initial reconstructed volume 621. The projection metal masks generated in step 714 can be used for multiple steps in generating a digital volume that has metal-artifacts reduced, including the harmonic inpainting of step 650 and the harmonic blending of step 690 in FIG. 6.

In step 720, the X-ray imaging system aborts the current metal artifact reduction process, and reconstruction, filtering, and/or other processes are performed normally on initial reconstructed volume 621.

Harmonic Inpainting of Projections

In conventional approaches, inpainting of 2D projection images, such as 2D projection metal masks 641 shown in FIG. 6, is performed with linear one-dimensional interpolation. Such inpainting creates both intra-projection discontinuities (i.e., between neighboring rows inside the same 2D projection) and inter-projection discontinuities (i.e., between corresponding rows of pixels in adjacent projections. Such discontinuities create significant visual artifacts in a final reconstructed volume, even though image information blocked by metal objects has been inpainted. According to various embodiments, a harmonic inpainting process improves intra-projection and inter-projection discontinuities in pixel values, which reduces visual artifacts that normally result from inpainting. One such embodiment is described below in conjunction with FIGS. 8-11.

Figure 8:
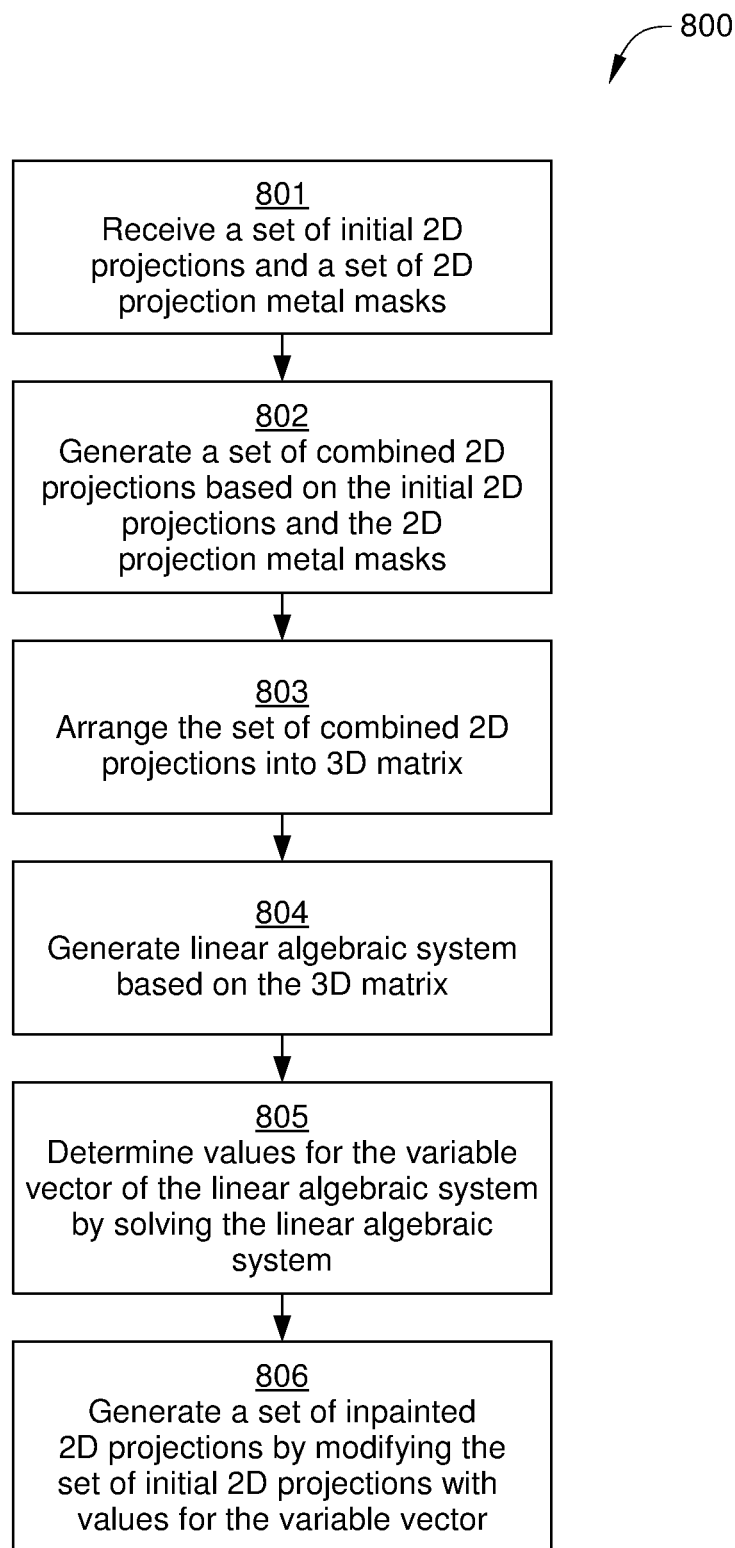
FIG. 8 sets forth a flowchart of a computer-implemented process for inpainting 2D projections of a region of patient anatomy, according to one or more embodiments.

FIG. 8 sets forth a flowchart of a computer-implemented process 800 for inpainting 2D projections of a region of patient anatomy, according to one or more embodiments. Computer-implemented process 800 can be implemented as part of an imaging-only process, or in conjunction with radiation therapy, such as IGRT, stereotactic radiosurgery (SRS), and the like. Computer-implemented process 800 may include one or more operations, functions, or actions as illustrated by one or more of blocks 801-806. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although computer-implemented process 800 is described in conjunction with the X-ray imaging system described herein as part of radiation therapy system 100 and FIGS. 1-6, persons skilled in the art will understand that any suitably configured X-ray imaging system is within the scope of the present embodiments.

In step 801, the X-ray imaging system of radiation therapy system 100 receives a set of initial 2D projections and a set of 2D projection metal masks for a reconstructed digital volume, such as acquired 2D projection images 611 and 2D projection metal masks 641 for initial reconstructed volume 621.

In step 802, the X-ray imaging system generates a set of combined 2D projections based on acquired 2D projection images 611 and 2D projection metal masks 641. In some embodiments, each combined 2D projection is generated based on a corresponding acquired 2D projection images 611 and a corresponding 2D projection metal masks 641. Generally, for a particular combined 2D projection, the corresponding acquired 2D projection images 611 and a corresponding 2D projection metal masks 641 each represent a projection from the same projection angle. One embodiment of a combined 2D projection generated from an acquired 2D projection image 611 and a 2D projection metal mask 641 is illustrated in FIG. 9.

Figure 9:
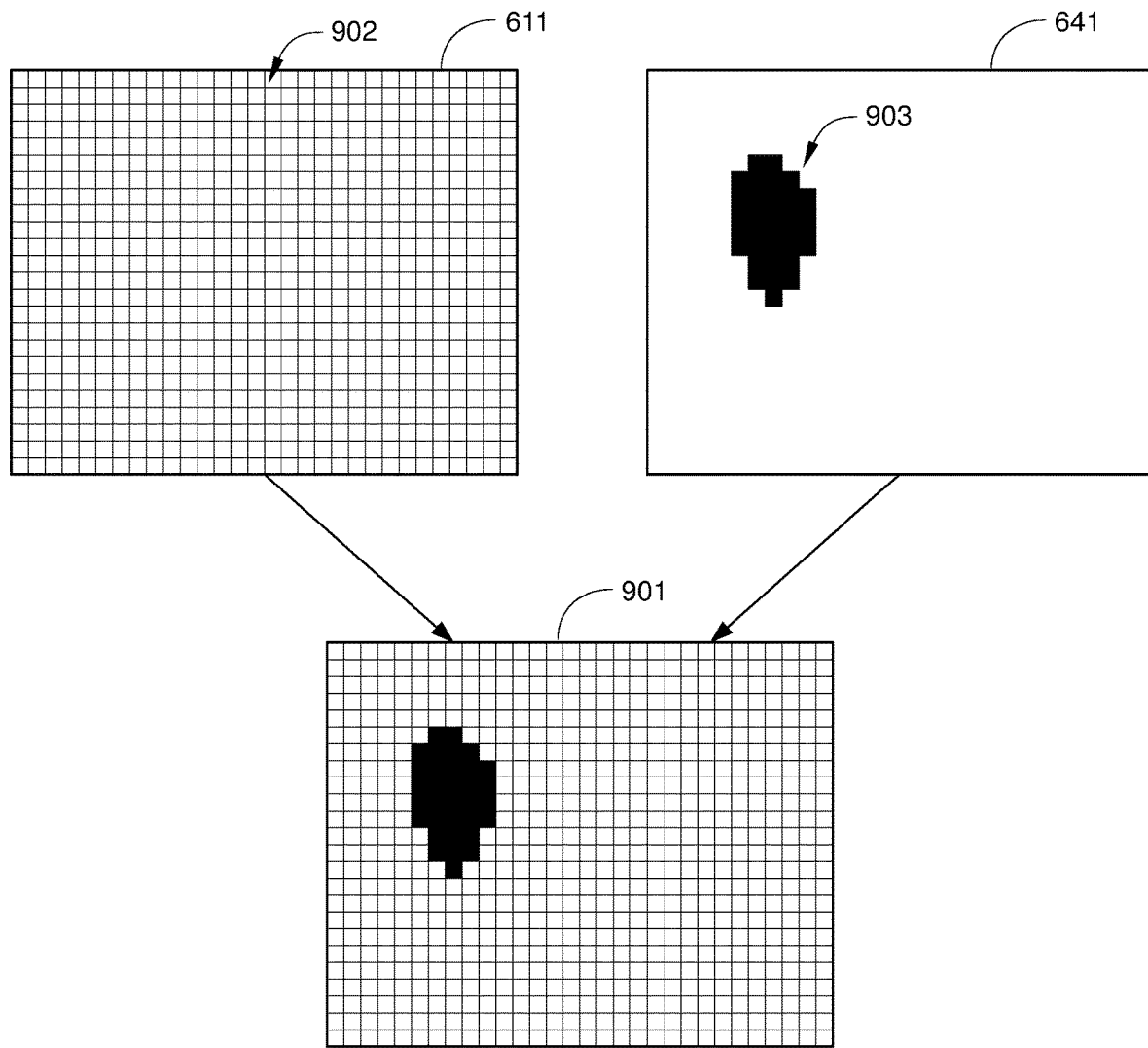
FIG. 9 schematically illustrates an acquired 2D projection image being combined with a 2D projection metal mask to form a combined 2D projection, according to various embodiments.

FIG. 9 schematically illustrates an acquired 2D projection image 611 being combined with a 2D projection metal mask 641 to form a combined 2D projection 901, according to various embodiments. As shown, acquired 2D projection image 611 includes a plurality of pixels 902 that each have a pixel value associated therewith, and 2D projection metal mask 641 includes location information 903 that indicates pixels that are blocked by metal object 501 during the forward projection process of step 640. Combined 2D projection 901 includes pixels 902 of acquired 2D projection image 611, except in pixel locations that correspond to location information 903 of 2D projection metal mask 641.

Returning to FIG. 8, in step 803, the X-ray imaging system arranges the set of combined 2D projections 901 into an array in projection space. For example, in some embodiments, the array of combined 2D projections are arranged in a 3D matrix or stack. In addition, the combined 2D projections 901 are sequentially ordered in the 3D matrix. Thus, in such embodiments, the combined 2D projection 901 that is generated from an acquired 2D projection image 611 and a 2D projection metal mask 641 that are each associated with a first projection angle is sequenced as the first 2D projection 901 in the 3D matrix, the combined 2D projection 901 that is generated from an acquired 2D projection image 611 and a 2D projection metal mask 641 that are each associated with a second projection angle is sequenced as the second 2D projection 901 in the 3D matrix, and so on. One embodiment of a 3D matrix of a combined 2D projections is illustrated in FIG. 10.

Figure 10:
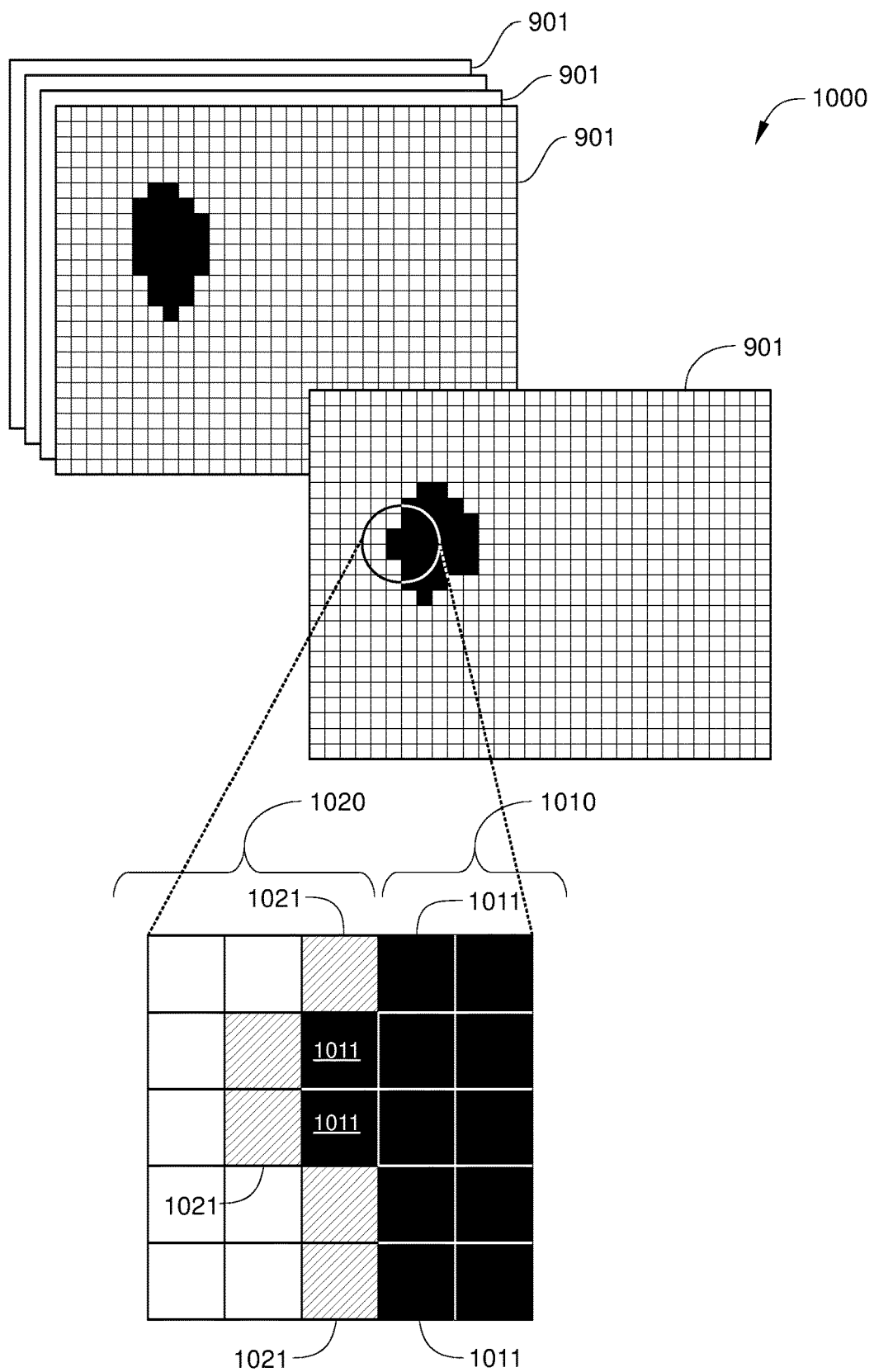
FIG. 10 schematically illustrates a 3D matrix, according to various embodiments.

FIG. 10 schematically illustrates a 3D matrix 1000 of combined 2D projections 901, according to various embodiments. In the embodiment illustrated in FIG. 10, array 1000 includes five combined 2D projections 901. In practice, 3D matrix 1000 can include many more than five combined 2D projections 901. As a series of 2D images arranged in three dimensions, 3D matrix 1000 forms a 3D array of image data that is analogous to a 2D CT sinogram. That is, while a CT sinogram extends a plurality of one-dimensional sets of image data into two dimensions by arranging the plurality of one-dimensional sets of data in a planar array, 3D matrix 1000 arranges a plurality of two-dimensional sets of image data associated with each of the different 2D projections in a 3D matrix or "stack".

As shown, each combined 2D projection 901 includes mask pixels (black) 1010 and image pixels 1020. Image pixels 1020 each have a pixel value (not shown) associated therewith. By contrast, each mask pixel 1010 indicates a location of a pixel that is blocked by a metal object (such as metal object 501 in FIG. 5), and therefore is inpainted during computer-implemented process 800. Image pixels 1020 include mask-bordering pixels 1021 (cross-hatched), which are pixels that are adjacent to one or more mask pixels 1010. Mask pixels 1010 include mask-edge pixels 1011, which are adjacent to one or more image pixels 1020. Generally, each mask-bordering pixel 1021 is adjacent to at least one mask-edge pixel 1011 in projection space. In the instance illustrated in FIG. 10, mask-bordering pixels 1021 are shown to be adjacent to mask pixels 1010 within the same combined 2D projection 901. In other instances, mask-bordering pixels 1021 can be adjacent to a mask pixel 1010 in a different combined 2D projection 901 within 3D matrix 1000. One such embodiment is illustrated in FIG. 11.

Figure 11:
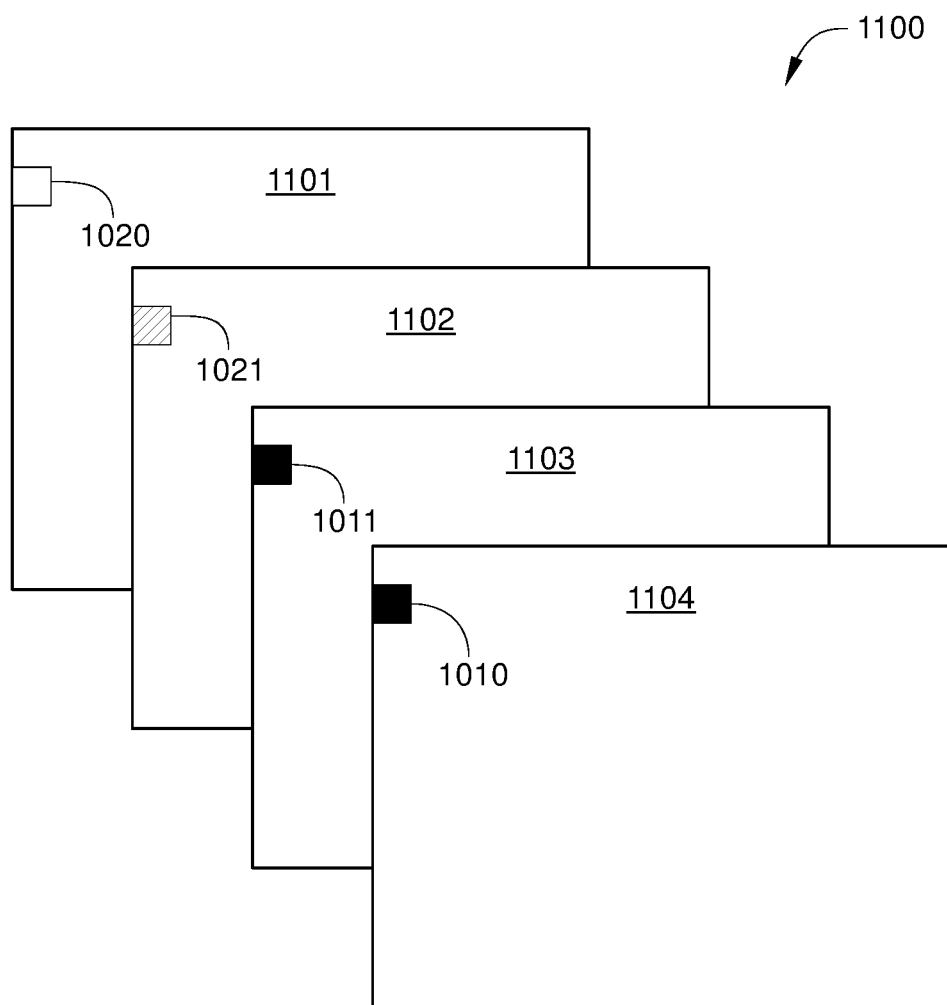
FIG. 11 schematically illustrates a portion of a 3D matrix and inter-projection pixels that are adjacent to each other, according to various embodiments.

FIG. 11 schematically illustrates a portion 1100 of 3D matrix 1000 and inter-projection pixels that are adjacent to each other, according to various embodiments. In the embodiment illustrated in FIG. 11, portion 1100 includes a first combined 2D projection 1101, a second combined 2D projection 1102, a third combined 2D projection 1103, and a fourth combined 2D projection 1104. As shown, second combined 2D projection 1102 includes a mask-bordering pixel 1021 (cross-hatched) that is adjacent (in projection space) to a corresponding mask-edge pixel 1011 that is included in third combined 2D projection 1103. In addition, first combined 2D projection 1101 includes an image pixel 1020 that is adjacent in projection space to a corresponding mask-bordering pixel 1021 in second combined 2D projection 1102, and fourth combined 2D projection 1104 includes a mask pixel 1010 that is adjacent to a corresponding mask-edge pixel 1011 that is included in third combined 2D projection 1103.

Returning to FIG. 8, in step 804, the X-ray imaging system generates a linear algebraic system based on array 1000. In some embodiments, the X-ray imaging system generates the linear algebraic system by applying a harmonic function to a domain represented by pixels included in array 1000, which is an array in projection space of a set of combined 2D projections 901. Specifically, in such embodiments, array 1000 is a 3D stack of combined 2D projections 901 that represents an image f. Thus, in such embodiments, Equation 2 is applied to the pixels included in array 1000:

$$\nabla^2 f = 0 \qquad (2)$$

In some embodiments, the X-ray imaging system generates the linear algebraic system by solving a discretized form of Equation 2 over the domain represented by the pixels of the image, for example via the method of finite differences. In such embodiments, Equation 2 is solved over the unknown part of the image, i.e., mask pixels 1010 in FIGS. 10 and 11, using the values from known regions as the boundary condition, i.e., mask-bordering pixels 1021 in FIGS. 10 and 11. In such embodiments, Equation 2 ensures continuity and smoothness of pixel values at the edges of the inpainted portions of each combined 2D projection. Further, because Equation 2 is solved for the domain represented by the mask pixels 1010 of all combined 2D projections 901 simultaneously, continuity and smoothness of pixel values between combined 2D projections 901 is also ensured. Thus, intra-projection and inter-projection discontinuities in pixel values are reduced. Specifically, in the harmonic inpainting process of computer-implemented process 800, when mask pixels of combined 2D projections 901 are inpainted with new pixel values, a change in slope of a pixel value associated with a mask-edge pixel is constrained to equal a change in slope of pixel value associated with an adjacent mask-bordering pixel. It is noted that the mask-edge pixel and the mask-bordering pixel are adjacent in projection space, and therefore can be included in the same combined 2D projection 901 (as shown in FIG. 10) or each can be included in different (but adjacent) combined 2D projections 901 (as shown in FIG. 11).

In some embodiments, in step 804, a linear algebraic system (a system of linear equations) is employed having the form [A][x]=[b], where [A] is a coefficient matrix of the linear algebraic system, [x] is a variable vector of the linear algebraic system, and [b] is a constant vector of the linear algebraic system. In such embodiments, the size of [A] and [b] is based on the number of mask pixels 1010 to be inpainted in array 1000. In such embodiments, values for [A] and [b] can be assembled using a 7-point finite difference method. For example, in one such embodiment, a 3D Laplacian kernel of size 3×3×3 kernels having 7 non-zero values is employed to generate values for [A] and [b]. A method of generating a linear algebraic system by applying a harmonic function to a domain of pixels is described in detail in: "On surface completion and image inpainting by biharmonic functions: Numerical aspects," S. B. Damelin, N. S. Hoang (2018), International Journal of Mathematics and Mathematical Sciences, 2018.

In step 805, the X-ray imaging system determines values for variable vector [x] of the linear algebraic system by solving the linear algebraic system. In some embodiments, values for variable vector [x] of the linear algebraic system are computed via a conjugate gradient method.

In step 806, the X-ray imaging system generates a set of inpainted 2D projections (e.g., 2D inpainted projections 651) by modifying the set of acquired 2D projection images 611 with the values for the variable vector determined in step 805. In step 806, pixels modified with the values for the variable vector are indicated by location information for mask pixels 1010, which may be included in 2D projection metal masks 641.

Example Computing Device

Figure 12:
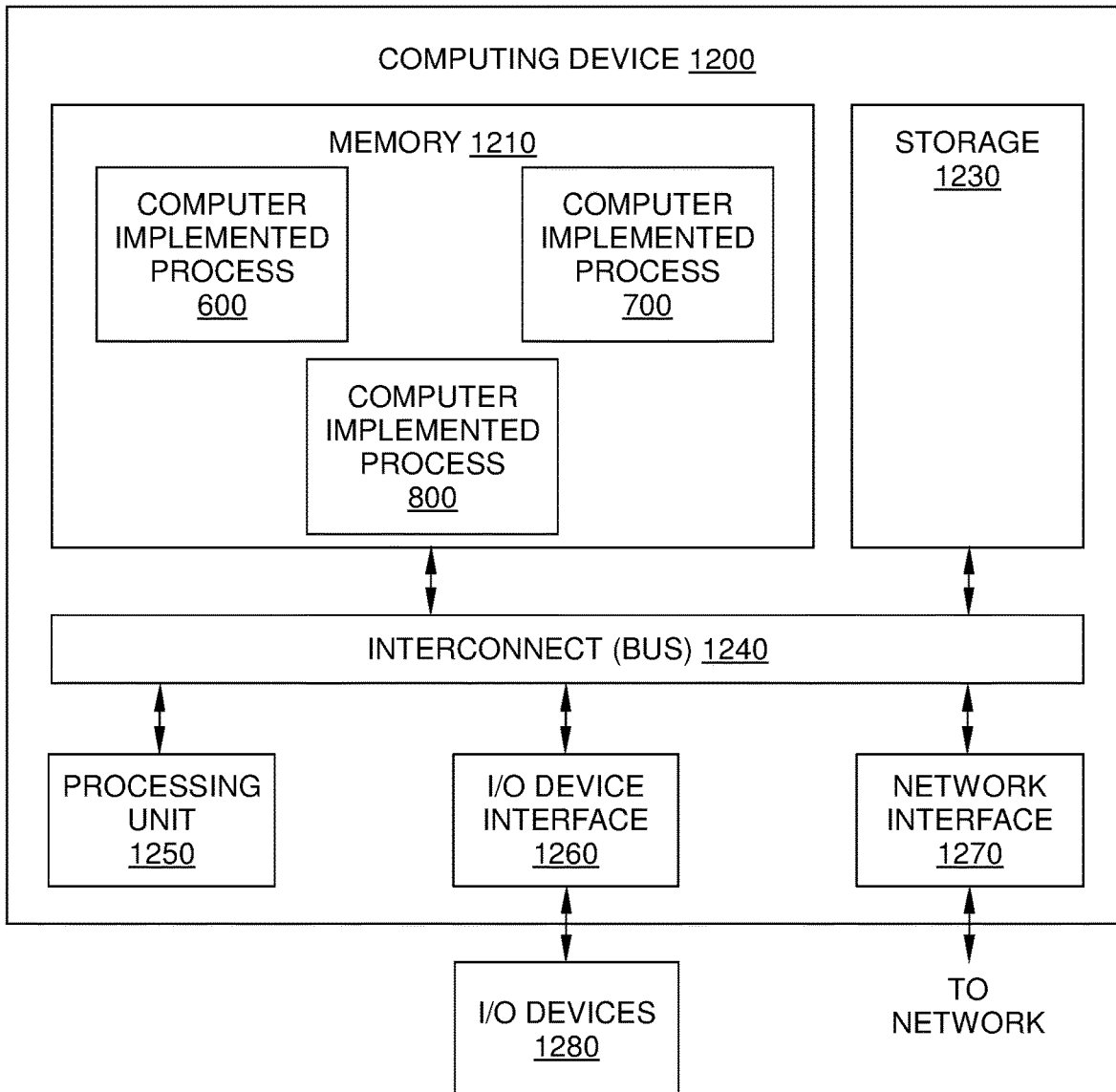
FIG. 12 is an illustration of a computing device configured to perform various embodiments.

FIG. 12 is an illustration of computing device 1200 configured to perform various embodiments of the present disclosure. For example, in some embodiments, computing device 1200 can be implemented as image acquisition and treatment control computer 106 and/or remote control console 110 in FIG. 1. Computing device 1200 may be a desktop computer, a laptop computer, a smart phone, or any other type of computing device suitable for practicing one or more embodiments of the present disclosure. In operation, computing device 1200 is configured to execute instructions associated with computer-implemented process 600, computer-implemented process 700, and/or computer-implemented process 800 as described herein. It is noted that the computing device described herein is illustrative and that any other technically feasible configurations fall within the scope of the present disclosure.

As shown, computing device 1200 includes, without limitation, an interconnect (bus) 1240 that connects a processing unit 1250, an input/output (I/O) device interface 1260 coupled to input/output (I/O) devices 1280, memory 1210, a storage 1230, and a network interface 1270. Processing unit 1250 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 1250 may be any technically feasible hardware unit capable of processing data and/or executing software applications, including computer-implemented process 600, computer-implemented process 700, and/or computer-implemented process 800.

I/O devices 1280 may include devices capable of providing input, such as a keyboard, a mouse, a touch-sensitive screen, and so forth, as well as devices capable of providing output, such as a display device and the like. Additionally, I/O devices 1280 may include devices capable of both receiving input and providing output, such as a touchscreen, a universal serial bus (USB) port, and so forth. I/O devices 1280 may be configured to receive various types of input from an end-user of computing device 1200, and to also provide various types of output to the end-user of computing device 1200, such as displayed digital images or digital videos. In some embodiments, one or more of I/O devices 1280 are configured to couple computing device 1200 to a network.

Memory 1210 may include a random access memory (RAM) module, a flash memory unit, or any other type of memory unit or combination thereof. Processing unit 1250, I/O device interface 1260, and network interface 1270 are configured to read data from and write data to memory 1210. Memory 1210 includes various software programs that can be executed by processor 1250 and application data associated with said software programs, including computer-implemented process 600, computer-implemented process 700, and/or computer-implemented process 800.

Example Computer Program Product

Figure 13:
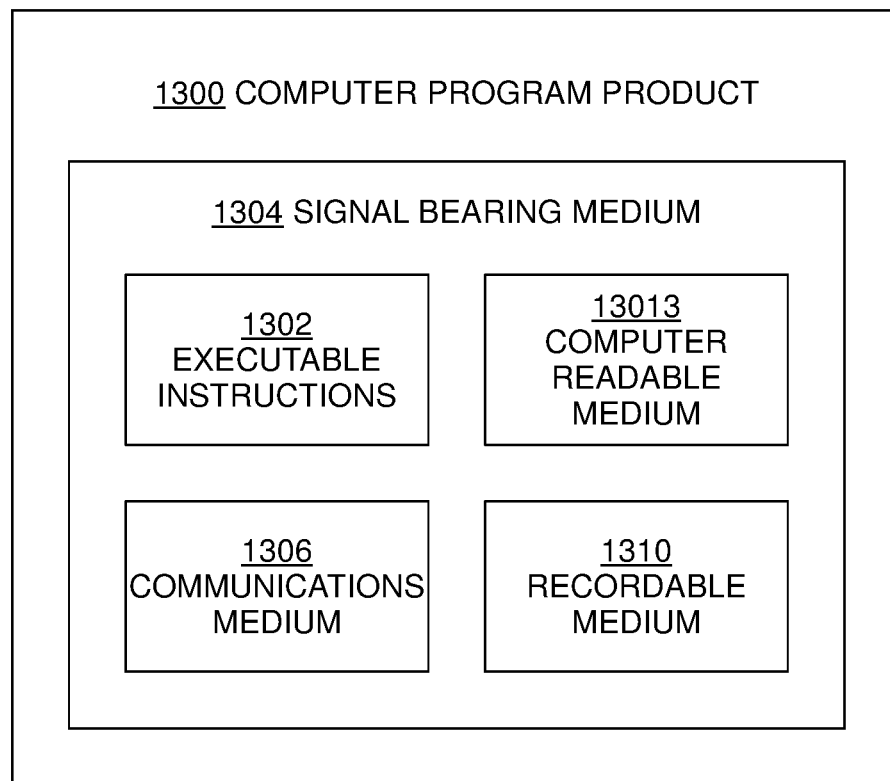
FIG. 13 is a block diagram of an illustrative embodiment of a computer program product for implementing one or more embodiments.

FIG. 13 is a block diagram of an illustrative embodiment of a computer program product 1300 for implementing a method for segmenting an image, according to one or more embodiments of the present disclosure. Computer program product 1300 may include a signal bearing medium 1304. Signal bearing medium 1304 may include one or more sets of executable instructions 1302 that, when executed by, for example, a processor of a computing device, may provide at least the functionality described above with respect to FIGS. 1-11.

In some implementations, signal bearing medium 1304 may encompass a non-transitory computer readable medium 1308, such as, but not limited to, a hard disk drive, a Compact Disc (CD), a Digital Video Disk (DVD), a digital tape, memory, etc. In some implementations, signal bearing medium 1304 may encompass a recordable medium 1310, such as, but not limited to, memory, read/write (R/W) CDs, R/W DVDs, etc. In some implementations, signal bearing medium 1304 may encompass a communications medium 1306, such as, but not limited to, a digital and/or an analog communication medium (e.g., a fiber optic cable, a waveguide, a wired communications link, a wireless communication link, etc.). Computer program product 1300 may be recorded on non-transitory computer readable medium 1308 or another similar recordable medium 1310.

In sum, embodiments described herein reduce and/or eliminate visual artifacts that occur in the reconstruction of a volume that includes one or more significant metal objects. Further, in some instances, the embodiments reveal structures previously obscured by such visual artifacts. Thus, the embodiments improve the perceived image quality of CBCT-based reconstructions and, in some instances improve accuracy in differentiating tissue types in a reconstructed CBCT image. Such improvements over prior art techniques may be employed in adaptive planning and/or during radiation therapy.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A computer-implemented method for modifying X-ray projection images of a subject region, the method comprising:
generating a set of combined two-dimensional (2D) projections of a subject region, based on a set of initial 2D projections of the subject region and a set of 2D projection metal masks for the subject region, wherein each combined 2D projection includes one or more mask-bordering pixels and one or more mask-edge pixels;
arranging the set of combined 2D projections sequentially to form a three-dimensional (3D) matrix;
based on the 3D matrix, generating a linear algebraic system for determining pixel values for pixels indicated in the set of 2D projection metal masks, wherein a first change in slope of pixel value associated with a mask-edge pixel of a combined 2D projection is constrained to equal a second change in slope of pixel value associated with a mask-bordering pixel of a combined 2D projection, and wherein the mask-bordering pixel is adjacent to the mask-edge pixel;

determining values for a variable vector of the linear algebraic system, wherein each element of the variable vector represents an inpainted pixel value; and generating a set of inpainted 2D projections by modifying the initial 2D projections with values for the variable vector.

2. The computer-implemented method of claim 1, wherein the mask-border pixel is included in a first combined 2D projection in the set of combined 2D projections and the mask-edge pixel is included in a second combined 2D projection in the set of combined 2D projections that is adjacent to the first combined 2D projection in the 3D matrix.

3. The computer-implemented method of claim 1, wherein the mask-border pixel is included in a first combined 2D projection in the set of combined 2D projections and the mask-edge pixel is included in the first combined 2D projection and is adjacent to the mask-border pixel within the first combined 2D projection.

4. The computer-implemented method of claim 1, wherein generating the linear algebraic system comprises applying a harmonic function to a domain represented by pixels included in the 3D matrix of the set of combined 2D projections.

5. The computer-implemented method of claim 4, wherein the pixels included in the 3D matrix form a 3D matrix of image data.

6. The computer-implemented method of claim 4, wherein generating the linear algebraic system further comprises solving a discretized form of the harmonic function via a finite differences method.

7. The computer-implemented method of claim 1, wherein determining values for the variable vector of the linear algebraic system comprises computing the values for the variable vector via a conjugate gradient method.

8. The computer-implemented method of claim 1, wherein generating the set of combined 2D projections of the subject region comprises modifying the initial 2D projections with location information from the set of 2D projection metal masks that indicates one or more mask pixels.

9. The computer-implemented method of claim 1, wherein the set of 2D projection metal masks includes location information for one or more mask pixels and one or more mask-edge pixels.

10. The computer-implemented method of claim 9, wherein modifying the initial 2D projections with values for the variable vector comprises applying the values for the variable vector to pixels indicated by the location information.

11. The computer-implemented method of claim 1, wherein the set of initial 2D projections of the subject region include X-ray projection images of the subject region.

12. The computer-implemented method of claim 1, further comprising, generating a reconstructed volume based on the set of inpainted 2D projections.

13. The computer-implemented method of claim 1, further comprising:

generating a non-binary mask based on a final 3D metal object mask and a reconstructed volume of the subject region; and generating a final reconstructed digital volume of the subject region based on the non-binary mask, the reconstructed volume of the subject region, and a low-artifact reconstructed volume of the subject region.

14. The computer-implemented method of claim 13, wherein the reconstructed volume of the subject region is generated using the set of initial 2D projections of the subject region.

15. The computer-implemented method of claim 13, wherein generating the final reconstructed digital volume based on the non-binary mask comprises, for each edge voxel of a metal object in the reconstructed volume, determining a value that is based on an image value from the reconstructed volume, an image value from the low-artifact reconstructed volume, and a value from the non-binary mask.

16. The computer-implemented method of claim 15, wherein the final 3D metal object mask includes location information associated with each edge voxel of the metal object.

17. The computer-implemented method of claim 13, further comprising generating the low-artifact reconstructed volume based on low-artifact 2D projections of the subject region.

18. The computer-implemented method of claim 17, wherein the low-artifact 2D projections are based on the set of inpainted 2D projections.

19. The computer-implemented method of claim 13, wherein:

the reconstructed volume includes a first visual artifact caused by the presence of a metal object in the reconstructed volume;

the low-artifact reconstructed volume includes a second visual artifact that corresponds to the first artifact; and the second visual artifact is reduced in visual prominence relative to the first visual artifact.

20. A non-transitory computer readable medium storing instructions that, when executed by a processor, cause the processor to perform the steps of:

generating a set of combined two-dimensional (2D) projections of a subject region, based on a set of initial 2D projections of the subject region and a set of 2D projection metal masks for the subject region, wherein each combined 2D projection includes one or more mask-bordering pixels and one or more mask-edge pixels;

arranging set of combined 2D projections sequentially to form a three-dimensional (3D) matrix;

based on the 3D matrix, generating a linear algebraic system for determining pixel values for pixels indicated in the set of 2D projection metal masks, wherein a first change in slope of pixel value associated with a mask-edge pixel of a combined 2D projection is constrained to equal a second change in slope of pixel value associated with a mask-bordering pixel of a combined 2D projection, and wherein the mask-bordering pixel is adjacent to the mask-edge pixel;

determining values for a variable vector of the linear algebraic system, wherein each element of the variable vector represents an inpainted pixel value; and generating a set of inpainted 2D projections by modifying the initial 2D projections with values for the variable vector.

* * * * *